United States Patent
O'Neil et al.

(10) Patent No.: US 10,646,350 B2
(45) Date of Patent: May 12, 2020

(54) MULTI-SEGMENT LATERAL CAGES ADAPTED TO FLEX SUBSTANTIALLY IN THE CORONAL PLANE

(71) Applicant: DePuy Synthes Products, Inc., Raynham, MA (US)

(72) Inventors: Michael J. O'Neil, West Barnstable, MA (US); Douglas Raymond, Bridgewater, MA (US); Jonathan Bellas, Bridgewater, MA (US); Andrew Dooris, Raynham, MA (US); Alexander Grinberg, Auburndale, MA (US); Derek Shaw, Attleboro, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/692,061

(22) Filed: Aug. 31, 2017

(65) Prior Publication Data

US 2017/0360455 A1 Dec. 21, 2017

Related U.S. Application Data

(63) Continuation of application No. 13/163,517, filed on Jun. 17, 2011, now Pat. No. 9,763,678.

(Continued)

(51) Int. Cl.
*A61F 2/44* (2006.01)
*A61F 2/46* (2006.01)
(Continued)

(52) U.S. Cl.
CPC ........ *A61F 2/4455* (2013.01); *A61B 17/1659* (2013.01); *A61B 17/1671* (2013.01);
(Continued)

(58) Field of Classification Search
CPC .... A61F 2/4455; A61F 2/4425; A61F 2/4611; A61F 2002/4415; A61F 2002/4475; A61F 2002/448
See application file for complete search history.

(56) References Cited

U.S. PATENT DOCUMENTS

| | | |
|---|---|---|
| 4,105,034 A | 8/1978 | Shalaby |
| 4,130,639 A | 12/1978 | Shalaby |

(Continued)

FOREIGN PATENT DOCUMENTS

| | | |
|---|---|---|
| DE | 19710392 | 7/1999 |
| DE | 10357960 | 7/2005 |

(Continued)

OTHER PUBLICATIONS

Vandorpe, "Biodegradable Polyphosphazenes for Biomedical Applications"; *Handbook of Biodegradable Polymers*; 1997; pp. 161-182; Hardwood Academic Press.

(Continued)

*Primary Examiner* — Ellen C Hammond

(57) ABSTRACT

The present invention concerns several fusion devices and methods for laterally inserting a fusion device at an initial trajectory that is not parallel to the disc space. Each fusion device incorporates components that enable flexing, bending or pivoting of the device during its final approach to the prepared disc space.

1 Claim, 35 Drawing Sheets

Related U.S. Application Data

(60) Provisional application No. 61/385,985, filed on Sep. 24, 2010, provisional application No. 61/410,177, filed on Nov. 4, 2010.

(51) Int. Cl.
| | |
|---|---|
| *A61B 17/16* | (2006.01) |
| *A61B 17/17* | (2006.01) |
| *A61M 29/02* | (2006.01) |
| *A61F 2/30* | (2006.01) |
| *A61B 5/00* | (2006.01) |
| *A61B 17/02* | (2006.01) |
| *A61B 17/34* | (2006.01) |
| *A61M 25/00* | (2006.01) |
| *A61M 25/01* | (2006.01) |

(52) U.S. Cl.
CPC ...... *A61B 17/1757* (2013.01); *A61F 2/30771* (2013.01); *A61F 2/446* (2013.01); *A61F 2/447* (2013.01); *A61F 2/4425* (2013.01); *A61F 2/4611* (2013.01); *A61F 2/4637* (2013.01); *A61M 29/02* (2013.01); *A61B 5/4893* (2013.01); *A61B 2017/0256* (2013.01); *A61B 2017/3433* (2013.01); *A61F 2/4465* (2013.01); *A61F 2/4603* (2013.01); *A61F 2002/30326* (2013.01); *A61F 2002/30523* (2013.01); *A61F 2002/30593* (2013.01); *A61F 2002/443* (2013.01); *A61M 25/0054* (2013.01); *A61M 25/0133* (2013.01)

(56) References Cited

U.S. PATENT DOCUMENTS

| | | |
|---|---|---|
| 4,140,678 A | 2/1979 | Shalaby |
| 4,141,087 A | 2/1979 | Shalaby |
| 4,205,399 A | 6/1980 | Shalaby |
| 4,208,511 A | 6/1980 | Shalaby |
| 4,538,612 A | 9/1985 | Patrick, Jr. |
| 4,834,757 A | 5/1989 | Brantigan |
| 4,863,476 A | 9/1989 | Shepperd |
| 4,995,200 A | 2/1991 | Eberhart |
| 5,006,121 A | 4/1991 | Hafeli |
| 5,019,082 A | 5/1991 | Frey |
| 5,123,926 A | 6/1992 | Piahsrodi |
| 5,133,719 A | 7/1992 | Winston |
| 5,163,939 A | 11/1992 | Winston |
| 5,169,402 A | 12/1992 | Elloy |
| 5,171,278 A | 12/1992 | Pisharodi |
| 5,217,475 A | 6/1993 | Kuber |
| 5,250,061 A | 10/1993 | Michelson |
| 5,320,644 A | 6/1994 | Baumgartner |
| 5,342,365 A | 8/1994 | Waldman |
| 5,387,215 A | 2/1995 | Fisher |
| 5,390,683 A | 2/1995 | Pisharodi |
| 5,454,815 A | 10/1995 | Geisser |
| 5,454,827 A | 10/1995 | Aust |
| 5,464,929 A | 11/1995 | Bezwada |
| 5,522,899 A | 6/1996 | Michelson |
| 5,540,693 A | 7/1996 | Fisher |
| 5,554,191 A | 9/1996 | Lahille |
| 5,595,751 A | 1/1997 | Bezwada |
| 5,597,579 A | 1/1997 | Bezwada |
| 5,601,561 A | 2/1997 | Terry |
| 5,607,687 A | 3/1997 | Bezwada |
| 5,618,552 A | 4/1997 | Bezwada |
| 5,620,698 A | 4/1997 | Bezwada |
| 5,645,850 A | 7/1997 | Bezwada |
| 5,648,088 A | 7/1997 | Bezwada |
| 5,658,335 A | 8/1997 | Allen |
| 5,665,122 A | 9/1997 | Kambin |
| 5,693,100 A | 12/1997 | Pisharodi |
| 5,698,213 A | 12/1997 | Jamiolkowski |
| 5,700,583 A | 12/1997 | Jamiolkowski |
| 5,725,531 A | 3/1998 | Shapiro |
| 5,857,995 A | 1/1999 | Thomas |
| 5,859,150 A | 1/1999 | Jamiolkowski |
| 5,865,848 A | 2/1999 | Baker |
| 5,916,228 A | 6/1999 | Ripich |
| 5,916,267 A | 6/1999 | Tienboon |
| 5,925,056 A | 7/1999 | Thomas |
| 5,976,187 A | 11/1999 | Richelsoph |
| 5,980,522 A | 11/1999 | Koros |
| 6,039,761 A | 3/2000 | Li |
| 6,045,579 A | 4/2000 | Hochshuler et al. |
| 6,053,922 A | 4/2000 | Krause |
| 6,056,763 A | 5/2000 | Parsons |
| 6,066,175 A | 5/2000 | Henderson |
| 6,080,158 A | 6/2000 | Lin |
| 6,106,557 A | 8/2000 | Robioneck |
| 6,120,508 A | 9/2000 | Grunig |
| 6,126,689 A | 10/2000 | Brett |
| 6,139,558 A | 10/2000 | Wagner |
| 6,176,882 B1 | 1/2001 | Biedermann |
| 6,241,733 B1 | 6/2001 | Nicholson |
| 6,251,140 B1 | 6/2001 | Marino |
| 6,258,093 B1 | 7/2001 | Edwards |
| 6,296,644 B1 | 10/2001 | Saurat |
| D450,676 S | 11/2001 | Huttner |
| 6,332,894 B1 | 12/2001 | Stalcup |
| 6,342,074 B1 | 1/2002 | Simpson |
| 6,387,130 B1 | 5/2002 | Stone |
| 6,398,793 B1 | 6/2002 | McGuire |
| 6,409,766 B1 | 6/2002 | Brett |
| 6,413,278 B1 | 7/2002 | Marchosky |
| 6,436,101 B1 | 8/2002 | Hamada |
| 6,447,518 B1 | 9/2002 | Krause |
| 6,579,318 B2 | 6/2003 | Ogilvie |
| 6,595,998 B2 | 7/2003 | Johnson et al. |
| 6,610,066 B2 | 8/2003 | Dinger |
| 6,635,060 B2 | 10/2003 | Hanson |
| RE38,335 E | 11/2003 | Aust |
| 6,641,582 B1 | 11/2003 | Hanson |
| 6,660,004 B2 | 12/2003 | Barker |
| 6,733,535 B2 | 5/2004 | Michelson |
| 6,755,837 B2 | 6/2004 | Ebner |
| 6,758,847 B2 | 7/2004 | Maguire |
| 6,764,491 B2 | 7/2004 | Frey |
| 6,835,208 B2 | 12/2004 | Marchosky |
| 6,840,941 B2 | 1/2005 | Rogers |
| 6,852,127 B2 | 2/2005 | Ogilvie |
| 6,878,167 B2 | 4/2005 | Ferree |
| 6,949,108 B2 | 9/2005 | Holmes |
| 6,966,912 B2 | 11/2005 | Michelson |
| 7,018,415 B1 | 3/2006 | McKay |
| 7,060,073 B2 | 6/2006 | Frey |
| 7,063,725 B2 | 6/2006 | Foley |
| 7,070,598 B2 | 7/2006 | Lim |
| 7,087,053 B2 | 8/2006 | Vanney |
| 7,087,055 B2 | 8/2006 | Lim |
| 7,089,063 B2 | 8/2006 | Lesh |
| 7,125,424 B2 | 10/2006 | Banick |
| 7,156,877 B2 | 1/2007 | Lotz |
| 7,226,482 B2 | 6/2007 | Messerli |
| 7,326,248 B2 | 2/2008 | Michelson |
| 7,351,262 B2 | 4/2008 | Bindseil |
| 7,406,775 B2 | 8/2008 | Funk |
| 7,470,273 B2 | 12/2008 | Dougherty-Shah |
| 7,491,237 B2 | 2/2009 | Randall |
| 7,503,920 B2 | 3/2009 | Siegal |
| 7,572,279 B2 | 8/2009 | Jackson |
| 7,575,580 B2 | 8/2009 | Lim |
| 7,578,820 B2 | 8/2009 | Moore |
| 7,601,173 B2 | 10/2009 | Messerli |
| 7,618,458 B2 | 11/2009 | Biedermann |
| 7,625,377 B2 | 12/2009 | Veldhuizen |
| 7,625,394 B2 | 12/2009 | Molz, IV |
| 7,655,010 B2 | 2/2010 | Serhan et al. |
| 7,666,186 B2 | 2/2010 | Harp |
| 7,666,226 B2 | 2/2010 | Schaller |
| 7,670,374 B2 | 3/2010 | Schaller |
| 7,674,265 B2 | 3/2010 | Smith |

(56) References Cited

U.S. PATENT DOCUMENTS

| | | |
|---|---|---|
| 7,682,400 B2 | 3/2010 | Zwirkoski |
| 7,703,727 B2 | 4/2010 | Selness |
| 7,704,280 B2 | 4/2010 | Lechman |
| 7,731,751 B2 | 6/2010 | Butler |
| 7,763,028 B2 | 7/2010 | Lim |
| 7,763,038 B2 | 7/2010 | O'Brien |
| 7,771,473 B2 | 8/2010 | Thramann |
| 7,785,368 B2 | 8/2010 | Schaller |
| 7,799,081 B2 | 9/2010 | McKinley |
| 7,803,161 B2 | 9/2010 | Foley |
| 7,828,849 B2 | 11/2010 | Lim |
| 7,837,734 B2 | 11/2010 | Zucherman |
| 7,850,733 B2 | 12/2010 | Baynham |
| 7,918,874 B2 | 4/2011 | Siegal |
| 7,922,719 B2 | 4/2011 | Ralph |
| 7,938,857 B2 | 5/2011 | Garcia-Bengochea |
| 7,942,903 B2 | 5/2011 | Moskowitz |
| 7,963,967 B1 | 6/2011 | Woods |
| 8,007,535 B2 | 8/2011 | Hudgins |
| 8,012,212 B2 | 9/2011 | Link |
| 8,025,697 B2 | 9/2011 | McClellan, III |
| 8,034,110 B2 | 10/2011 | Garner et al. |
| 8,038,703 B2 | 10/2011 | Dobak, III |
| 8,043,293 B2 | 10/2011 | Warnick |
| 8,057,544 B2 | 11/2011 | Schaller |
| 8,105,382 B2 | 1/2012 | Olmos |
| 8,128,700 B2 | 3/2012 | Delurio |
| 8,206,423 B2 | 6/2012 | Siegal |
| 8,216,317 B2 | 7/2012 | Thibodeau |
| 8,241,364 B2 | 8/2012 | Hansell |
| 8,262,666 B2 | 9/2012 | Baynham |
| 8,267,939 B2 | 9/2012 | Cipoletti |
| 8,343,193 B2 | 1/2013 | Johnson et al. |
| 8,343,222 B2 | 1/2013 | Cope |
| 8,366,777 B2 | 2/2013 | Matthis |
| 8,382,842 B2 | 2/2013 | Greenhalgh et al. |
| 8,403,990 B2 | 3/2013 | Dryer et al. |
| 8,454,617 B2 | 6/2013 | Schaller et al. |
| 8,579,981 B2 | 11/2013 | Lim |
| 8,628,577 B1 | 1/2014 | Jimenez |
| 8,663,331 B2 | 3/2014 | McClellan, III |
| 8,740,954 B2 | 6/2014 | Gregory |
| 8,845,733 B2 | 9/2014 | O'Neil |
| 8,845,734 B2 | 9/2014 | O'Neil et al. |
| 8,920,506 B2 | 12/2014 | McGuckin, Jr. |
| 8,926,704 B2 | 1/2015 | Glerum et al. |
| 8,940,050 B2 | 1/2015 | Laurence |
| 8,961,609 B2 | 2/2015 | Schaller |
| 8,968,408 B2 | 3/2015 | Schaller et al. |
| 9,101,488 B2 | 8/2015 | Malandain |
| 9,101,491 B2 * | 8/2015 | Rodgers .............. A61F 2/447 |
| 9,101,492 B2 | 8/2015 | Mangione |
| 9,282,979 B2 | 3/2016 | O'Neil |
| 9,801,639 B2 | 10/2017 | O'Neil |
| 9,801,640 B2 | 10/2017 | O'Neil |
| 10,405,989 B2 | 9/2019 | O'Neil |
| 2002/0138078 A1 | 9/2002 | Chappuis |
| 2002/0143399 A1 | 10/2002 | Sutcliffe |
| 2002/0165550 A1 | 11/2002 | Frey et al. |
| 2002/0183758 A1 | 12/2002 | Middleton |
| 2003/0028251 A1 | 2/2003 | Matthews |
| 2003/0135275 A1 | 7/2003 | Garcia |
| 2003/0139812 A1 | 7/2003 | Garcia et al. |
| 2003/0191531 A1 | 10/2003 | Berry |
| 2004/0002761 A1 | 1/2004 | Rogers et al. |
| 2004/0030387 A1 | 2/2004 | Landry |
| 2004/0059337 A1 | 3/2004 | Hanson |
| 2004/0068269 A1 | 4/2004 | Bonati |
| 2004/0083000 A1 | 4/2004 | Keller |
| 2004/0087947 A1 | 5/2004 | Lim et al. |
| 2004/0102784 A1 | 5/2004 | Pasquet |
| 2004/0102846 A1 | 5/2004 | Keller |
| 2004/0127990 A1 | 7/2004 | Bartish |
| 2004/0147129 A1 | 7/2004 | Rolfson |
| 2004/0220668 A1 | 11/2004 | Eisermann |
| 2005/0038431 A1 | 2/2005 | Bartish |
| 2005/0096745 A1 | 5/2005 | Andre |
| 2005/0119752 A1 | 6/2005 | Williams et al. |
| 2005/0149034 A1 | 7/2005 | Assell |
| 2005/0165420 A1 | 7/2005 | Cha |
| 2005/0165484 A1 | 7/2005 | Ferree |
| 2005/0171541 A1 | 8/2005 | Boehm |
| 2005/0177173 A1 | 8/2005 | Aebi |
| 2005/0240193 A1 | 10/2005 | Layne |
| 2005/0261683 A1 | 11/2005 | Veldhuizen |
| 2005/0267463 A1 | 12/2005 | Vanney |
| 2006/0036244 A1 | 2/2006 | Spitler |
| 2006/0276902 A1 | 2/2006 | Zipnick |
| 2006/0058807 A1 | 3/2006 | Landry |
| 2006/0064101 A1 | 3/2006 | Arramon |
| 2006/0064102 A1 | 3/2006 | Ebner |
| 2006/0069436 A1 | 3/2006 | Sutton |
| 2006/0074429 A1 | 4/2006 | Ralph |
| 2006/0100622 A1 | 5/2006 | Jackson |
| 2006/0111715 A1 | 5/2006 | Jackson |
| 2006/0111728 A1 | 5/2006 | Abdou |
| 2006/0122701 A1 | 6/2006 | Kiester |
| 2006/0129244 A1 | 6/2006 | Ensign |
| 2006/0142858 A1 | 6/2006 | Colleran |
| 2006/0167547 A1 | 7/2006 | Suddaby |
| 2006/0189999 A1 | 8/2006 | Zwirkoski |
| 2006/0212118 A1 | 9/2006 | Abernathie |
| 2006/0229627 A1 | 10/2006 | Hunt |
| 2006/0229724 A1 | 10/2006 | Lechman |
| 2006/0235426 A1 | 10/2006 | Lim |
| 2006/0253120 A1 | 11/2006 | Anderson |
| 2006/0254784 A1 | 11/2006 | Hartmann et al. |
| 2006/0265077 A1 | 11/2006 | Zwirkoski |
| 2006/0293753 A1 | 12/2006 | Thramann |
| 2007/0055264 A1 | 3/2007 | Parmigiani |
| 2007/0055272 A1 | 3/2007 | Schaller |
| 2007/0067035 A1 | 3/2007 | Falahee |
| 2007/0093897 A1 | 4/2007 | Gerbec |
| 2007/0093901 A1 | 4/2007 | Grotz et al. |
| 2007/0142843 A1 | 6/2007 | Dye |
| 2007/0162132 A1 | 7/2007 | Messerli |
| 2007/0162138 A1 | 7/2007 | Heinz |
| 2007/0213737 A1 | 9/2007 | Schermerhorn |
| 2007/0213826 A1 | 9/2007 | Smith |
| 2007/0225726 A1 | 9/2007 | Dye |
| 2007/0225815 A1 | 9/2007 | Keith |
| 2007/0233130 A1 | 10/2007 | Suddaby |
| 2007/0250167 A1 | 10/2007 | Bray et al. |
| 2007/0260314 A1 | 11/2007 | Biyani |
| 2007/0270957 A1 | 11/2007 | Heinz |
| 2007/0270968 A1 | 11/2007 | Baynham |
| 2008/0027544 A1 | 1/2008 | Melkent |
| 2008/0027550 A1 | 1/2008 | Link |
| 2008/0045966 A1 | 2/2008 | Buttermann |
| 2008/0051890 A1 | 2/2008 | Waugh |
| 2008/0058933 A1 | 3/2008 | Garner |
| 2008/0065082 A1 | 3/2008 | Chang |
| 2008/0077150 A1 | 3/2008 | Nguyen |
| 2008/0077241 A1 | 3/2008 | Nguyen |
| 2008/0082173 A1 | 4/2008 | Delurio |
| 2008/0091211 A1 | 4/2008 | Gately |
| 2008/0097454 A1 | 4/2008 | DeRidder |
| 2008/0108990 A1 | 5/2008 | Mitchell |
| 2008/0119935 A1 | 5/2008 | Alvarez |
| 2008/0125865 A1 | 5/2008 | Abdelgany |
| 2008/0133012 A1 | 6/2008 | McGuckin |
| 2008/0140085 A1 | 6/2008 | Gately |
| 2008/0154379 A1 | 6/2008 | Steiner |
| 2008/0172128 A1 | 7/2008 | Perez-Cruet et al. |
| 2008/0208255 A1 | 8/2008 | Siegal |
| 2008/0221586 A1 | 9/2008 | Garcia-Bengochea |
| 2008/0221687 A1 | 9/2008 | Viker |
| 2008/0234732 A1 | 9/2008 | Landry |
| 2008/0234733 A1 | 9/2008 | Scrantz |
| 2008/0243126 A1 | 10/2008 | Gutierrez |
| 2008/0243255 A1 | 10/2008 | Butler |
| 2008/0249628 A1 * | 10/2008 | Altarac .............. A61F 2/4455 623/17.16 |
| 2008/0255563 A1 | 10/2008 | Farr |

(56) References Cited

U.S. PATENT DOCUMENTS

| | | |
|---|---|---|
| 2008/0255574 A1 | 10/2008 | Dye |
| 2008/0269904 A1 | 10/2008 | Voorhies |
| 2008/0312743 A1 | 12/2008 | Vila |
| 2009/0030423 A1 | 1/2009 | Puno |
| 2009/0054898 A1 | 2/2009 | Gleason |
| 2009/0054911 A1 | 2/2009 | Mueller |
| 2009/0062807 A1 | 3/2009 | Song |
| 2009/0076607 A1 | 3/2009 | Aalsma |
| 2009/0088789 A1 | 4/2009 | O'Neil |
| 2009/0112217 A1 | 4/2009 | Hester |
| 2009/0143859 A1 | 6/2009 | McClellan, III |
| 2009/0164016 A1 | 6/2009 | Georgy |
| 2009/0182431 A1 | 7/2009 | Butler |
| 2009/0192616 A1 | 7/2009 | Zielinski |
| 2009/0216234 A1 | 8/2009 | Farr |
| 2009/0221967 A1 | 9/2009 | Thommen |
| 2009/0234364 A1 | 9/2009 | Crook |
| 2009/0240335 A1 | 9/2009 | Arcenio |
| 2009/0276049 A1 | 11/2009 | Weiland |
| 2009/0299479 A1 | 12/2009 | Jones |
| 2010/0016968 A1 | 1/2010 | Moore |
| 2010/0030217 A1 | 2/2010 | Mitusina |
| 2010/0076502 A1 | 3/2010 | Guyer |
| 2010/0094422 A1 | 4/2010 | Hansell |
| 2010/0100098 A1 | 4/2010 | Norton |
| 2010/0100183 A1 | 4/2010 | Prewett |
| 2010/0125334 A1 | 5/2010 | Krueger |
| 2010/0161060 A1 | 6/2010 | Schaller |
| 2010/0174321 A1 | 7/2010 | Schaller |
| 2010/0185290 A1 | 7/2010 | Compton |
| 2010/0191241 A1 | 7/2010 | McCormack |
| 2010/0198263 A1 | 8/2010 | Siegal |
| 2010/0211076 A1 | 8/2010 | Germain |
| 2010/0211107 A1 | 8/2010 | Muhanna |
| 2010/0217269 A1 | 8/2010 | Landes |
| 2010/0234849 A1 | 9/2010 | Bouadi |
| 2010/0249935 A1 | 9/2010 | Slivka |
| 2010/0256768 A1 | 10/2010 | Lim |
| 2010/0274358 A1 | 10/2010 | Mueller et al. |
| 2010/0280619 A1 | 11/2010 | Yuan |
| 2010/0305700 A1 | 12/2010 | Ben-Arye |
| 2010/0305704 A1 | 12/2010 | Messerli |
| 2010/0331845 A1 | 12/2010 | Foley |
| 2011/0004216 A1 | 1/2011 | Amendola |
| 2011/0009970 A1 | 1/2011 | Puno |
| 2011/0029083 A1 | 2/2011 | Hynes |
| 2011/0029085 A1 | 2/2011 | Hynes |
| 2011/0035011 A1 | 2/2011 | Cain |
| 2011/0106260 A1 | 5/2011 | Laurence |
| 2011/0112586 A1 | 5/2011 | Guyer |
| 2011/0125266 A1 | 5/2011 | Rodgers |
| 2011/0190891 A1 | 8/2011 | Suh et al. |
| 2011/0276142 A1 | 11/2011 | Niemiec |
| 2011/0282459 A1 | 11/2011 | McClellan, III |
| 2011/0301712 A1 | 12/2011 | Palmatier et al. |
| 2011/0319898 A1 | 12/2011 | O'Neil |
| 2011/0319998 A1 | 12/2011 | O'Neil |
| 2011/0319999 A1 | 12/2011 | O'Neil |
| 2011/0320000 A1 | 12/2011 | O'Neil |
| 2012/0035730 A1 | 2/2012 | Spann |
| 2012/0165943 A1 | 6/2012 | Mangione |
| 2012/0209383 A1 | 8/2012 | Tsuang |
| 2012/0277877 A1 | 11/2012 | Smith |
| 2012/0310352 A1 | 12/2012 | DiMauro |
| 2013/0006362 A1 | 1/2013 | Biedermann |
| 2013/0023937 A1 | 1/2013 | Biedermann |
| 2013/0035762 A1 | 2/2013 | Siegal |
| 2013/0079790 A1 | 3/2013 | Stein |
| 2013/0109925 A1 | 5/2013 | Horton |
| 2013/0110239 A1 | 5/2013 | Siegal et al. |
| 2013/0116791 A1 | 5/2013 | Theofilos |
| 2013/0138214 A1 | 5/2013 | Greenhalgh |
| 2013/0150906 A1 | 6/2013 | Kerboul |
| 2013/0173004 A1 | 7/2013 | Greenhalgh |
| 2013/0190875 A1 | 7/2013 | Shulock |
| 2013/0238006 A1 | 9/2013 | O'Neil |
| 2013/0268077 A1 | 10/2013 | You |
| 2013/0310937 A1 | 11/2013 | Pimenta |
| 2014/0025170 A1 | 1/2014 | Lim |
| 2014/0039626 A1 | 2/2014 | Mitchell |
| 2014/0052259 A1 | 2/2014 | Garner et al. |
| 2014/0058512 A1 | 2/2014 | Petersheim |
| 2014/0058513 A1 | 2/2014 | Gahman |
| 2014/0172103 A1 | 6/2014 | O'Neil |
| 2014/0172105 A1 | 6/2014 | Frasier |
| 2015/0032212 A1 | 1/2015 | O'Neil |
| 2015/0094812 A1 | 4/2015 | Cain |
| 2015/0196400 A1 | 7/2015 | Dace |
| 2016/0038306 A1 | 2/2016 | Oneil |
| 2017/0128231 A1 | 5/2017 | O'Neil |
| 2018/0028200 A1 | 2/2018 | O'Neil |
| 2018/0036141 A1 | 2/2018 | O'Neil |

FOREIGN PATENT DOCUMENTS

| | | |
|---|---|---|
| EP | 609084 | 9/1997 |
| EP | 1283026 | 9/2003 |
| EP | 1405602 | 4/2004 |
| EP | 1308132 | 12/2006 |
| EP | 1829486 | 9/2007 |
| FR | 2874814 | 3/2006 |
| FR | 2948277 | 1/2011 |
| WO | WO 1992014423 | 9/1992 |
| WO | WO 1998034568 | 8/1998 |
| WO | WO 1999060956 | 12/1999 |
| WO | WO 1999063914 | 12/1999 |
| WO | WO 2000024343 | 5/2000 |
| WO | WO 200074605 | 12/2000 |
| WO | WO 2002003870 | 1/2002 |
| WO | WO 2003003951 | 1/2003 |
| WO | WO 2004030582 | 4/2004 |
| WO | WO 2004080316 | 9/2004 |
| WO | WO 2004069033 | 1/2005 |
| WO | WO 2005094297 | 10/2005 |
| WO | WO 2004080316 | 12/2005 |
| WO | WO 2006118944 | 11/2006 |
| WO | WO 2006044920 | 12/2006 |
| WO | WO 2007048012 | 4/2007 |
| WO | WO 2008005627 | 1/2008 |
| WO | WO 2006072941 | 7/2008 |
| WO | WO 2010011348 | 1/2010 |
| WO | WO 2010075555 | 10/2010 |
| WO | WO 2010121002 | 12/2010 |
| WO | WO 2011013047 | 4/2011 |
| WO | WO 2011060087 | 5/2011 |
| WO | WO 2012129197 | 9/2012 |
| WO | WO 2013149611 | 10/2013 |
| WO | WO 2012027490 | 3/2014 |
| WO | WO 2012103254 | 4/2014 |

OTHER PUBLICATIONS

Allcock, "Polyphosphazenes"; *The Encyclopedia of Polymer Science*; 1988; pp. 31-41; vol. 13; Wiley Intersciences, John Wiley & Sons.

Cohn, "Polymer Preprints"; *Journal of Biomaterials Research*; 1989; p. 498; Biomaterials Research Labortatory, Casali Institute of Applied Chemistry, Israel.

Cohn, "Biodegradable PEO/PLA Block Copolymers"; *Journal of Biomedical Materials Research*; 1988; pp. 993-1009; vol. 22; John Wiley & Sons, Inc.

Heller, "Poly (Otrho Esters)"; *Handbook of Biodegradable Polymers*; edited by Domb; et al; Hardwood Academic Press; 1997; pp. 99-118.

Kemnitzer, "Degradable Polymers Derived From the Amino Acid L-Tyrosine"; 1997; pp. 251-272; edited by Domb, et. al., Hardwood Academic Press.

Khoo, Axilif address spongy from the caudal approach. Minimally Invasive Correction of Grage I and II Isthmic Spondylolisthesis using AsiaLiF for L5/S1 Fusion, pp. 45-0123 Rev B Sep. 15, 2008.

U.S. Appl. No. 61/140,926, filed Dec. 26, 2008 Spann.

(56) References Cited

OTHER PUBLICATIONS

U.S. Appl. No. 61/178,315, filed May 14, 2009 Spann.

* cited by examiner

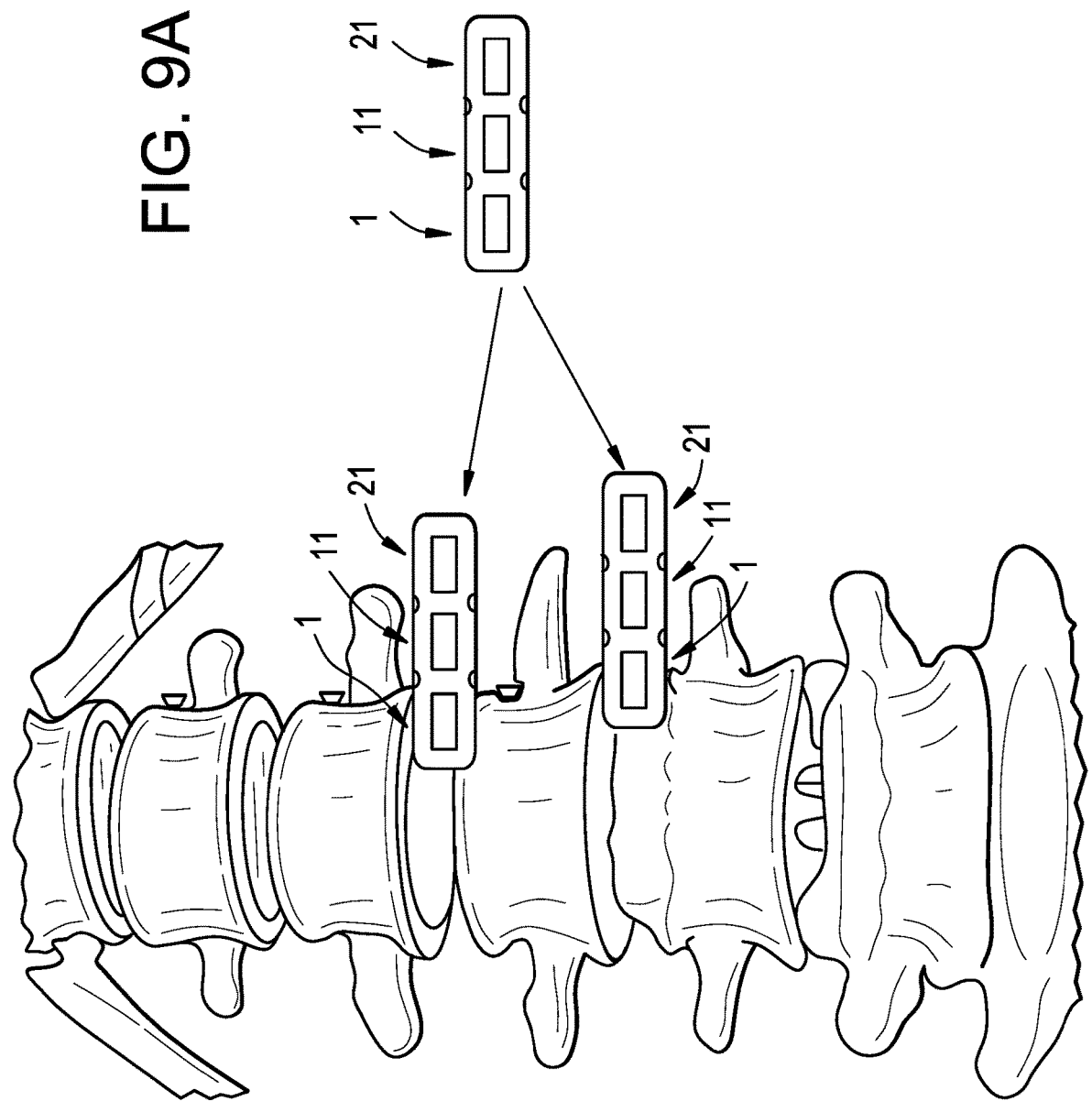

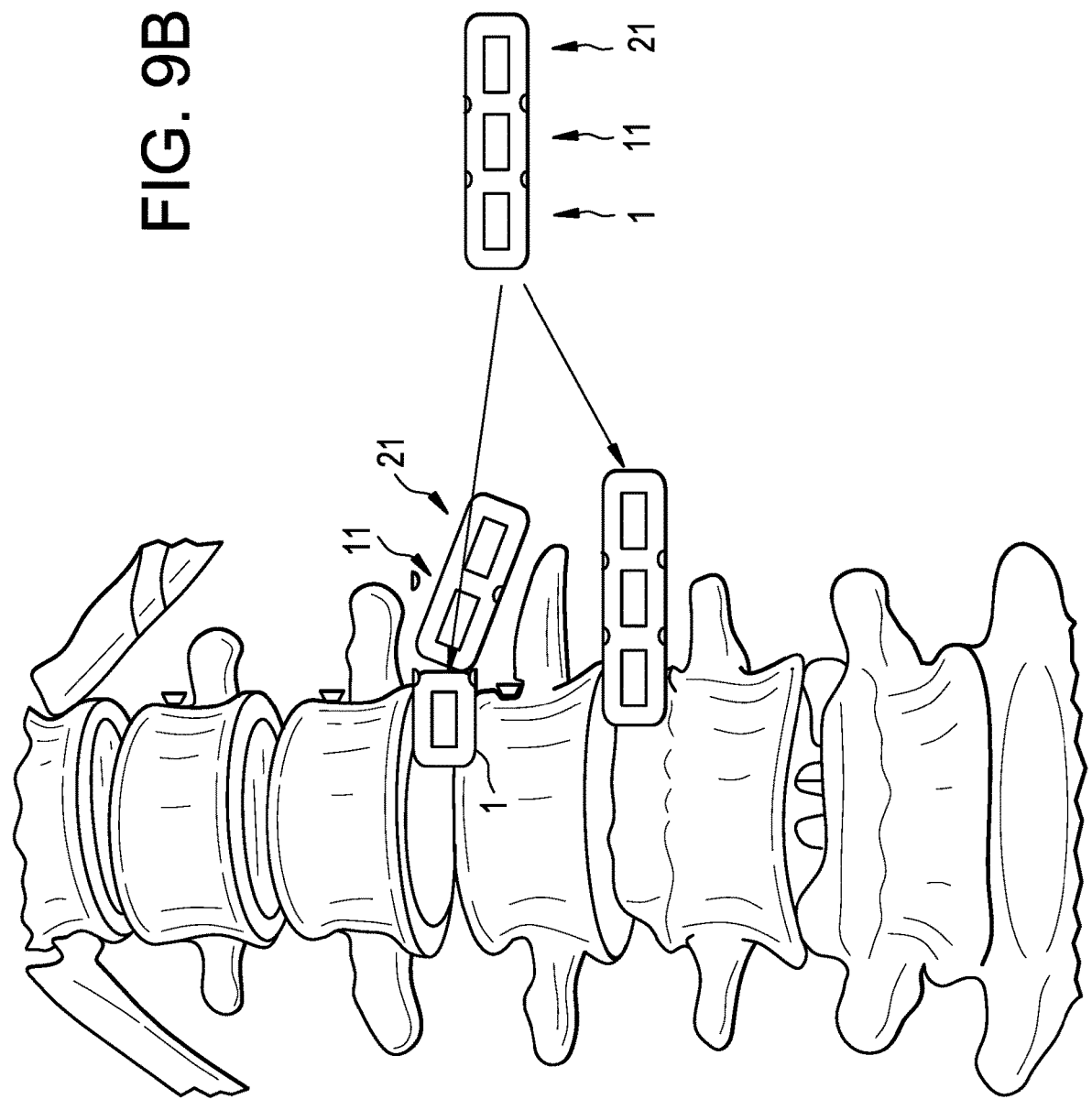

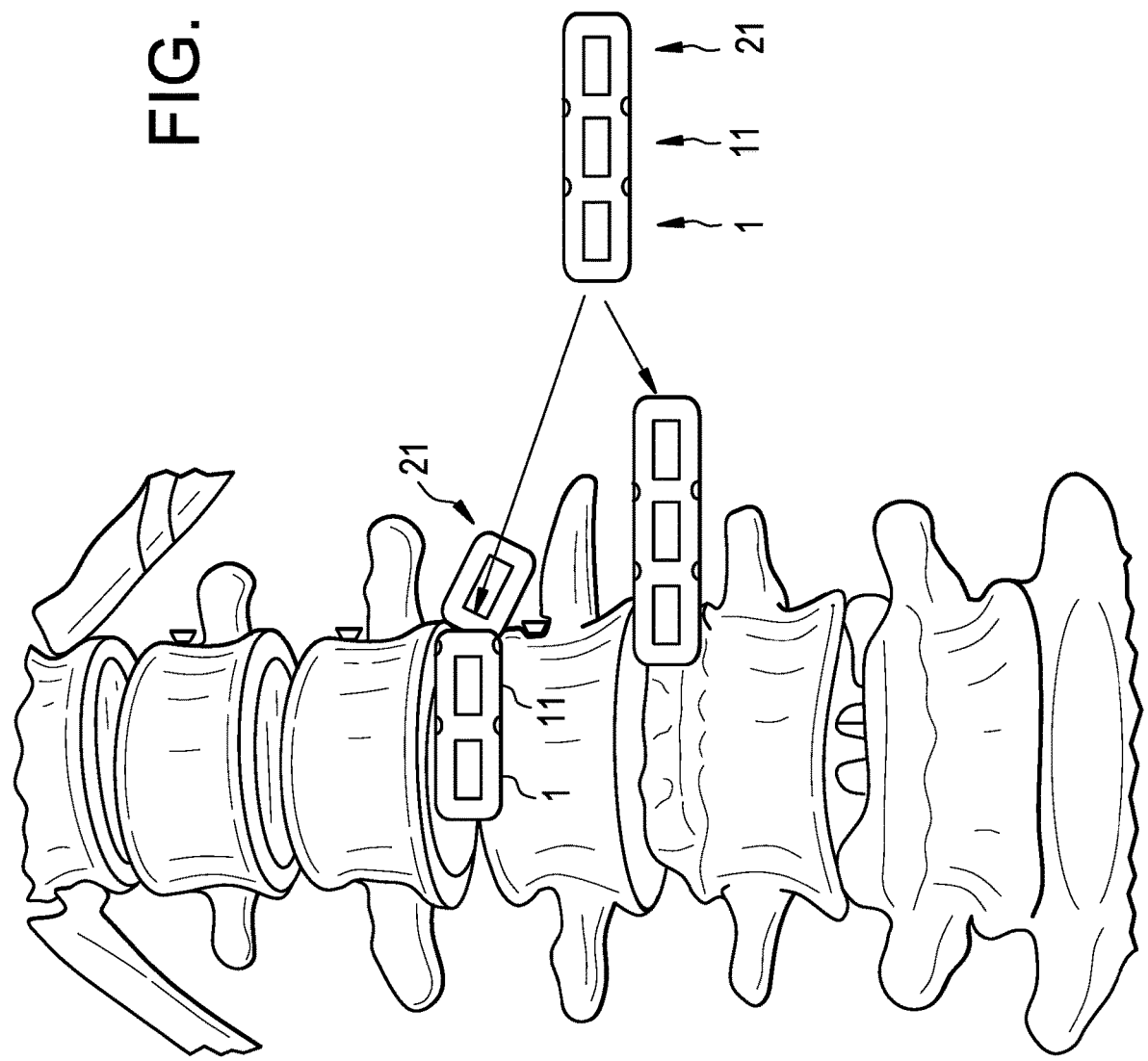

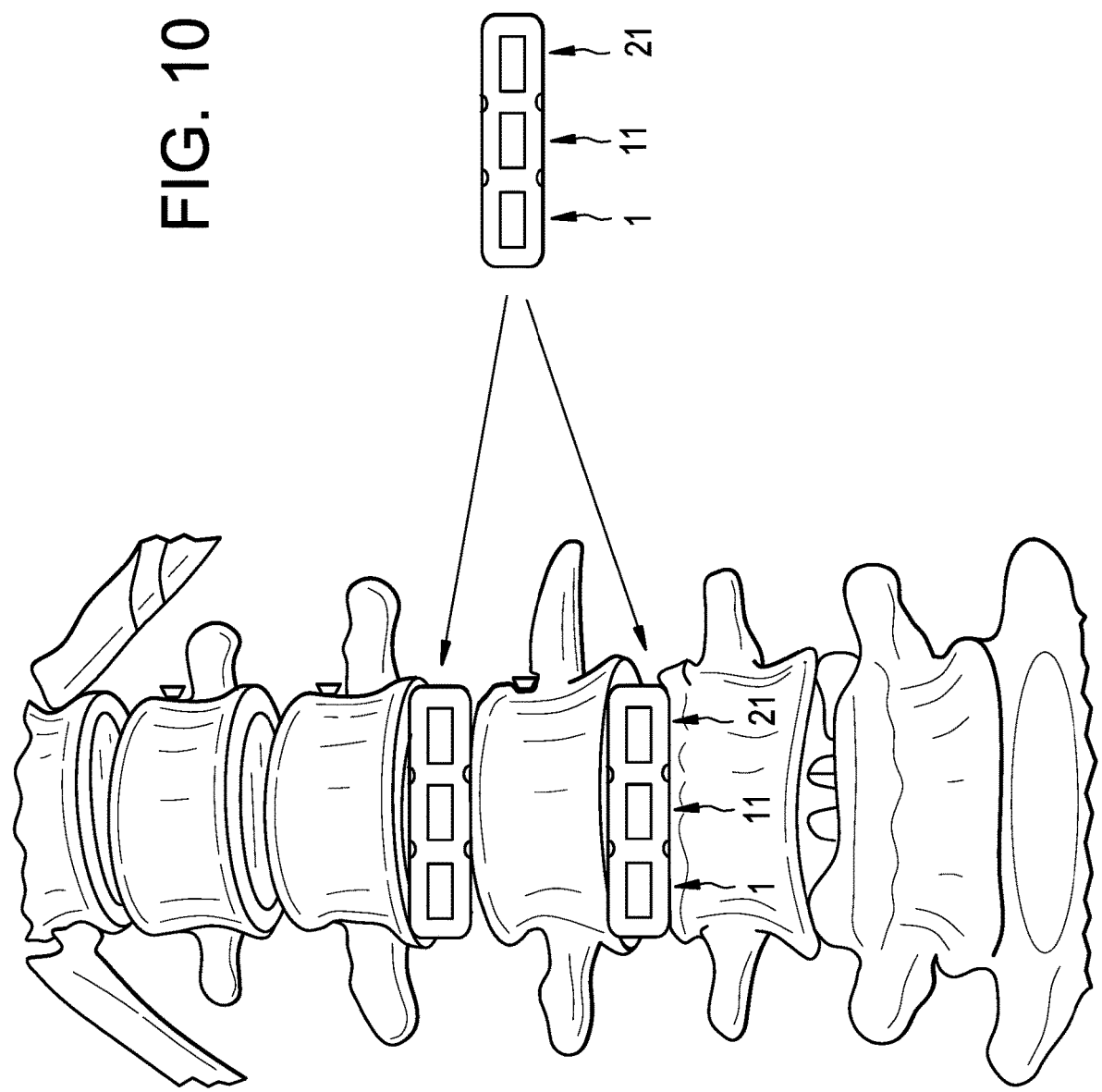

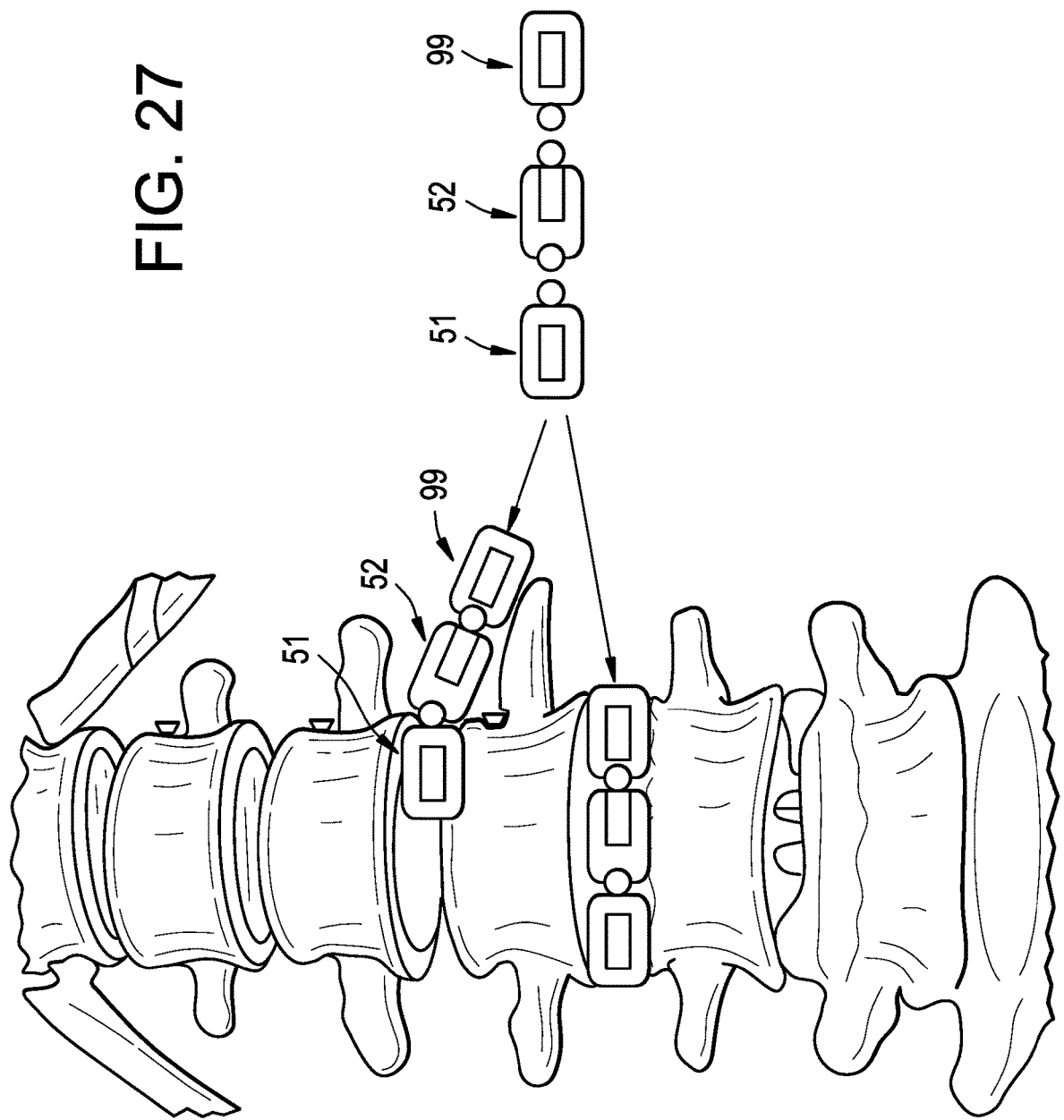

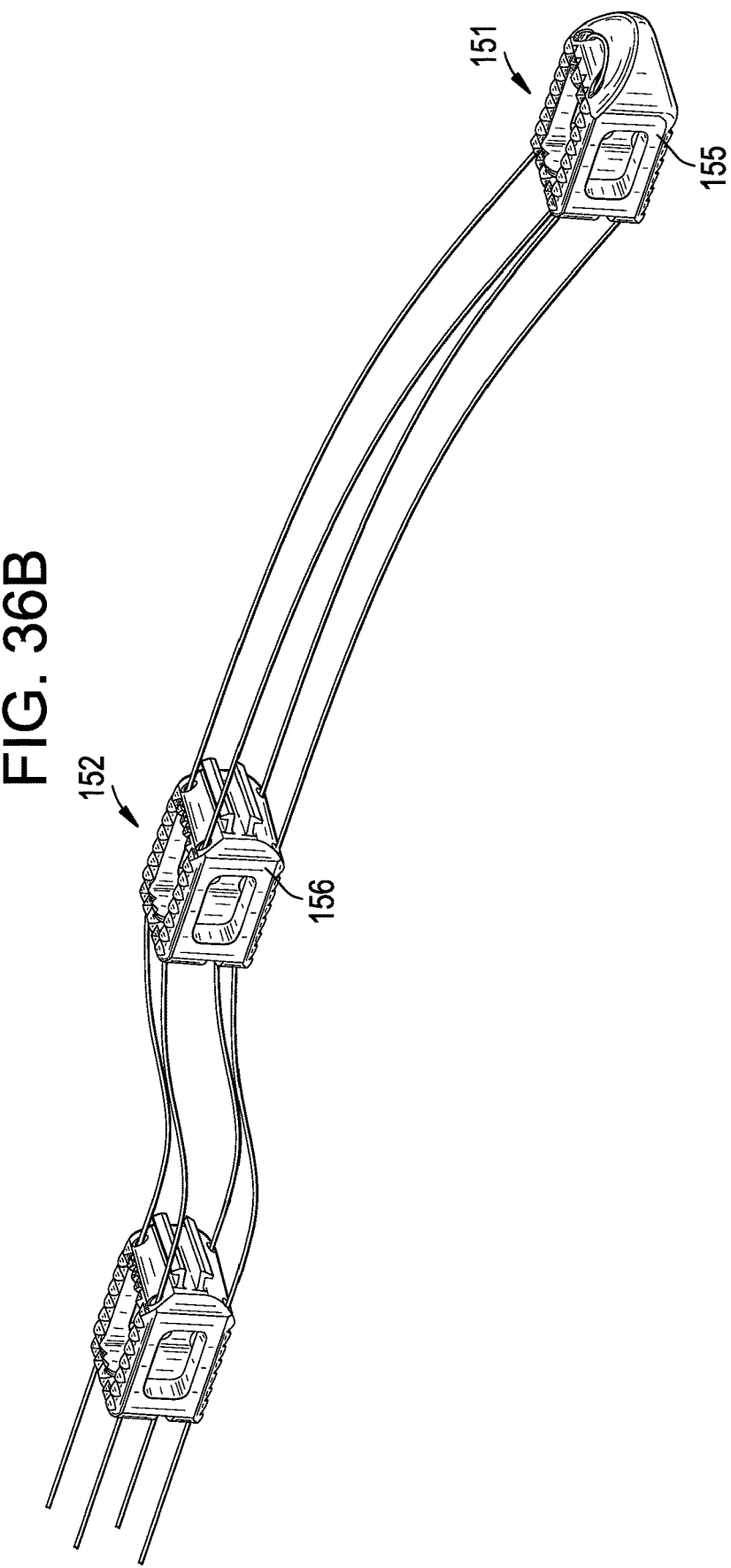

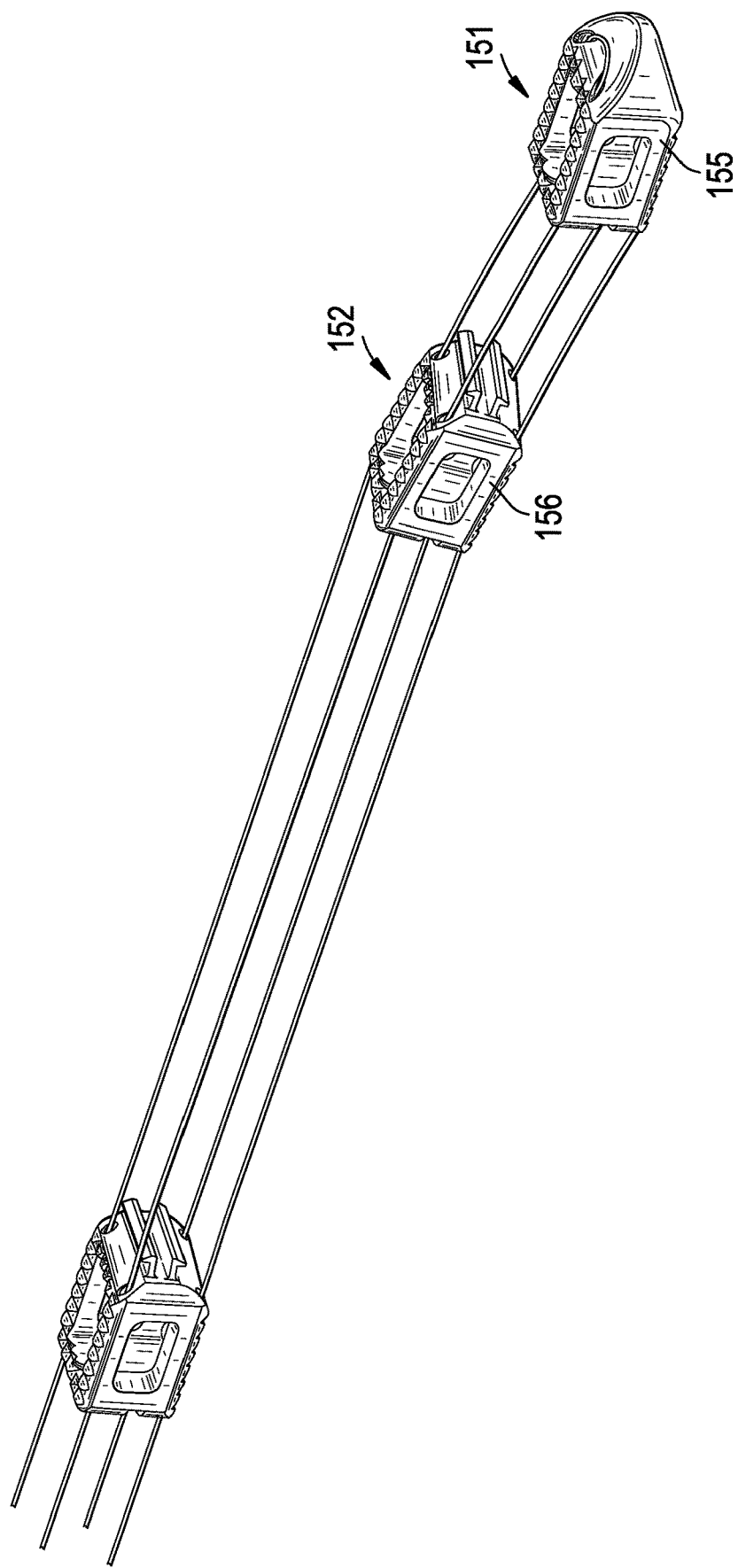

US 10,646,350 B2

MULTI-SEGMENT LATERAL CAGES ADAPTED TO FLEX SUBSTANTIALLY IN THE CORONAL PLANE

RELATED APPLICATIONS

This application is a continuation of and claims priority from co-pending patent application U.S. Ser. No. 13/163,517, entitled "Multi-Segment Lateral Cages adapted to Flex Substantially in the Coronal Plane", filed on Jun. 17, 2011 (O'Neil et al.) which claims priority from provisional application U.S. Ser. No. 61/385,958, filed Sep. 23, 2010, entitled Multi-Segment. Lateral Cages adapted to Flex Substantially in the Coronal Plane; and from provisional application U.S. Ser. No. 61/410,177 filed Nov. 4, 2010 entitled Multi-Segment Lateral Cages adapted to Flex Substantially in the Coronal Plane, the specifications of which are incorporated by reference in their entireties.

BACKGROUND OF THE INVENTION

The lateral access approach is frequently utilized to deliver interbody fusion cages to the lumbar spine. In comparison to conventional anterior or posterior approaches to the lumbar spine, the lateral approach is thought to minimize posterior and/or anterior tissue damage as well as reduce surgery time, associated blood loss, vascular damage and infection risk.

When multi-level access to the spine is provided through a single minimal access port, the insertion trajectory to the superior and inferior levels is not parallel to the vertebral endplates at those levels.

In addition, direct lateral access parallel to the L4/5 and L5/S1 levels is not achieved due to the presence of the iliac crest directly lateral to those levels. Accordingly, the angled trajectory required for lateral access to these lower levels risks the cages being implanted at a "malpositioned" angle that prevents balanced loading across the vertebral endplates and spine. This "malpositioned" access, associated endplate damage and device placement can initiate subsidence, loss of correction, collapse of the retracted disc space, and result in spinal instability. This may result in increased surgery time, a higher difficulty in insertion and muscle damage.

US2008-0133012 ("McGuckin") discloses a spinal implant having a series of sections or units hinged together and a balloon connected to at least some of the sections, the balloon having a curved configuration. The implant has a first delivery configuration and a second curved placement configuration, wherein it has a more linear configuration in the first delivery configuration than in the second curved configuration. The implant assumes the first delivery configuration during delivery to the disc space and maintains the curved configuration after placement within the disc space. The curved configuration can result from filling or expanding the balloon.

US2006-0142858 ("Colleran") discloses methods and apparatuses for maintaining spacing between neighboring vertebrae, while minimizing the size of the surgical opening required. In one embodiment, an expandable spinal implant is made having movable parts that can arranged so as to have a small maximum cross-sectional width so that the cage can be inserted through a smaller surgical opening and then expanded to a full size assembly between the vertebrae.

U.S. Pat. No. 6,387,130 ("Stone") discloses a method of positioning a plurality of intervertebral implants in a patient's intervertebral space, comprising: introducing an elongated member into the patient's intervertebral space; and sequentially advancing a plurality of intervertebral implants over the elongated member and into the patient's intervertebral space, the plurality of intervertebral implants each having at least one hole passing therethrough, with the elongated member received through the holes passing through each of the plurality of implants.

US Patent Publication No. 2008-0125865 (Custom Spine) discloses an intervertebral fusion device that articulates in the horizontal plane.

US Patent Publication No 2009-0062807 (Vermillion Technologies, LLC) discloses a method for performing percutaneous interbody preparation and placement of an interbody device from a posterolateral orientation via a cannulated, self-distracting tool with a guide mechanism.

US Patent Application 2011-0125266 (Rogers) discloses lateral cage that vertically flex.

SUMMARY OF THE INVENTION

The present invention concerns several fusion devices and methods for laterally inserting a fusion device at an initial trajectory that is not parallel to the disc space. Each fusion device incorporates components that enable flexing, bending or pivoting of the device during its final approach to the prepared disc space.

In one embodiment, these fusion devices may be delivered through a disc space access port having a linear longitudinal axis. Once the distal end of the fusion device is inserted through the linear port and into the edge of the disc space, additional force is applied to the device along the longitudinal axis of the proximal portion of the device. This additional force has the effect of flexing the device in the coronal plane. Continued application of force to the flexed device results in advance of the device into the disc space in an orientation that is parallel to the disc space. Therefore, in accordance with the present invention, there is provided) a method of implanting a flexible intervertebral fusion device in a disc space in a patient, comprising the steps of:
 a) creating an access path to the disc space wherein the access path is substantially linear and lies substantially in a coronal plane;
 b) advancing the intervertebral fusion device through the access path;
 c) partially inserting the intervertebral device into the disc space;
 d) applying a force to a proximal portion of the inserted device to bend the device in the coronal plane and thereby orient it substantially parallel to the disc space; and
 e) fully implanting the oriented intervertebral fusion device in the disc space.

Alternatively, these fusion devices may be delivered through a port that has an elbow in its distal portion. The elbowed shape of this port enables initial delivery of the cage from an incision location above the iliac crest and lateral to the spine, followed by linear advance of the fusion device in the coronal plane at a downward trajectory that is angled with respect to the disc space, and finally flexion of the fusion device in the coronal plane at the elbow so that it may initially enter the disc space with an orientation that is parallel to the disc space. Therefore, in accordance with the present invention, there is provided).
a method of implanting an intervertebral fusion device in a disc space in a patient, comprising the steps of:
 a) creating an access path to the disc space wherein the access path is substantially in a coronal plane and has an elbowed portion;

b) advancing the intervertebral fusion device through the access path, wherein the device bends substantially in a coronal plane while in the elbowed portion of the access path;

c) implanting the intervertebral fusion cage in the disc space.

In a first embodiment, there is provided a flexible intervertebral fusion device. These lateral devices are provided with one or more upper or lower flexion grooves (that make living hinges) that allow flexing in the coronal plane upon passage of the device into the disc space (or into the elbow of the port). The coronal flexion between the various cage segments allows angled advancement and parallel insertion to be accomplished. Following implantation the cage segments act as one fusion cage comprised of interconnected rigid spacers for spinal correction, graft delivery and fusion of the disc space.

The flexion grooves are typically of living hinge design, are provided in polymer-based cages, and may be customized to provide specific material properties and desired ranges of flexion. Desired ranges of flexion vary from 1 to 45 degrees and are dependent upon the number and location of cage segments. The depth and shape of a groove can sometimes range from 10% to 90% of the cage height, with the width of the groove typically ranging from 0.5 mm to 10 mm.

The leading distal edge of the device may be bulleted upon its upper and/or lower aspects to facilitate the device's initial placement into the disc space.

In some embodiments, the coronal flexibility in the fusion device is made by providing an intermediate, reduced height wall that substantially bisects the proximal and distal end walls of the fusion device. Therefore, in accordance with the present invention, there is provided a flexible lateral intervertebral fusion device comprising:

a) a first cage having an upper surface, a lower surface, anterior and posterior sidewalls therebetween, a proximal wall and a distal wall, b) a second cage having an upper surface, a lower surface, anterior and posterior sidewalls therebetween, a proximal wall and a distal wall, wherein the proximal wall of the first cage is integrally attached to the distal wall of the second cage by a flexible strut.

In a second embodiment, there is provided an intervertebral fusion device having linked cages.

In some embodiments, the flats of these cages engage each other to absorb the impaction force.

In some embodiments, cage components are linked by an articulating snap means that ensures that the device can have a substantially linear orientation during the insertion and advancement portions of the delivery and a substantially curved orientation during its passage into the disc space (or through the elbow portion of the port). In some embodiments thereof, the proximal end wall of a first cage is connected to the distal end wall of a second cage by an articulating joint (such as a hinge) that articulates substantially in the coronal plane. In some embodiments, the joint comprises a ball-and-socket connection, wherein one of the cages comprises the ball component and the other cage comprises the socket component. In some embodiments, the joint is a hinge that articulates substantially only in the coronal plane.

The articulating snap means interconnects the cage components and allows the cage components to flex upon insertion in a manner similar to the flexible cage invention discussed above. The interconnecting linkage can be a snap fit ball joint that allows for articulation in at least the coronal plane, but may also articulate in all planes. Alternatively, the linkage can be designed to limit motion to the coronal plane, as with a dovetail or tongue-and-groove connection.

The articulating linkage can be fixed by pins that both secure the segments and allow for imaging of the implant. The linked cage also allows for intra-operative selection and assembly of the cage component geometries based upon the desired level of correction or endplate geometry at a specific location. This can be advantageous for scoliosis correction or irregular endplates.

Therefore, in accordance with the present invention, there is provided a lateral intervertebral fusion device comprising first and second cages, each cage comprising:

a) an anterior wall, b) a posterior wall, c) proximal and distal end walls connecting the anterior and posterior walls wherein the proximal end wall of the first cage is connected to the distal end wall of the second cage by a joint that articulates substantially in the plane of the posterior wall.

In a preferred second embodiment, there is provided a linked fusion device in which a pair of cages are linked by a flexible tape provided on either an upper or lower bearing surface of the cages. The flexible tapes or wires interconnect the cage segments and provide for flexion of the cage segments upon insertion like that of the flexible cage segments disclosed above. Thus, this flexible tape ensures that the cage components are linearly oriented during linear advance of the device through the linear portion of the port, and flexed during their passage into the disc space (or through the elbowed portion of the port). The function of the tape is to provide a flexible connection between the separately manufactured cages, wherein the connection is capable of flexing upon application of a load. The advantage of using an adhesive tape is that the tape can be applied to the cages during the operative procedure, thereby allowing the surgeon to custom-design the fusion device to meet the needs of the particular patient.

The degree of pre-tension and/or material stiffness of the wire or tape can allow for varying levels of flexion in all planes. Although the tape can be placed on any external surface of a cage, it is preferably placed upon the superior and inferior aspects of the device in order to provide for a controlled amount of flexion in the coronal plane while accessing a non-parallel level.

In some embodiments, the tape or wire can be radiopaque. In other embodiments, the tape or wire can be resorbable to allow for controlled separation of the cage components, as controlled cage segment separation may prevent excessive load transfer in one specific location of the disc.

Therefore, in accordance with the present invention, there is provided an intervertebral fusion device comprising first, second and third cages and a flexible band, wherein each cage comprises:

a) an anterior wall, b) a posterior wall, c) proximal and distal end walls connecting the anterior and posterior walls, and wherein the flexible band runs from proximal end wall of the first cage, through the second cage and to the distal end of the third cage.

In some embodiments, the cage components are linked by a pretensioned wire through their centers.

In another embodiment, there is provided an intervertebral fusion device having tethered cage components. The cage components can be tethered together with a cord that passes through the proximal and distal end walls of each cage. The tether can also provide a method of advancing the subcomponents into the disc, which guide cage segments. This tether allows the cage components to assemble into a linear configuration during its initial passage through the linear portion of the port, and into a flexed configuration during its passage through the disc space (or through the elbowed portion of the port). Each cage component further has a portion of a securement means (such as a taper interlock) to fixedly join the cage components together once they have all reached the disc space. Preferably, the tether is selected from the group consisting of a cord, a suture, a wire tie, and a chain. The tether can include both advancement and securement features.

The interconnecting tether or suture can also provide a method to advance the subcomponents into the disc while allowing flexion between the various cage segments. The tether can be a simple cord or a suture, which is tensioned as desired. The tether can also be comprised of a wire tie design, or a chain with snaps that hold the cage components together.

Once all of the cage components have been assembled in situ, the tether can be removed from the patient. In other embodiments, the tether is made of a resorbable material so that it is gradually removed over time.

DESCRIPTION OF THE FIGURES

FIGS. 9a-9c and 10 disclose a method of implanting the flexible cage of the present invention.

FIG. 27 discloses a method of implanting the jointed device of the present invention.

FIGS. 36a-36g disclose a method of implanting the snap device of the present invention.

DETAILED DESCRIPTION OF THE INVENTION

Figure 1:
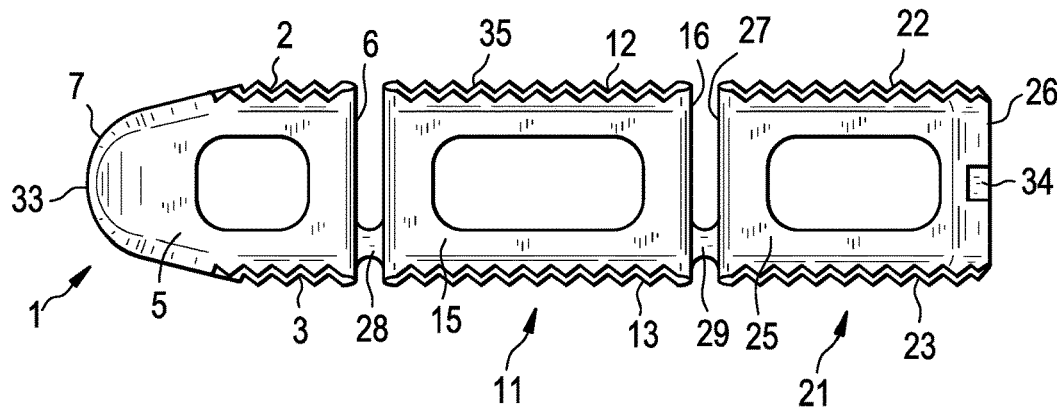
FIGS. 1-8 disclose various views of the flexible cage of the present invention.
Figure 2:
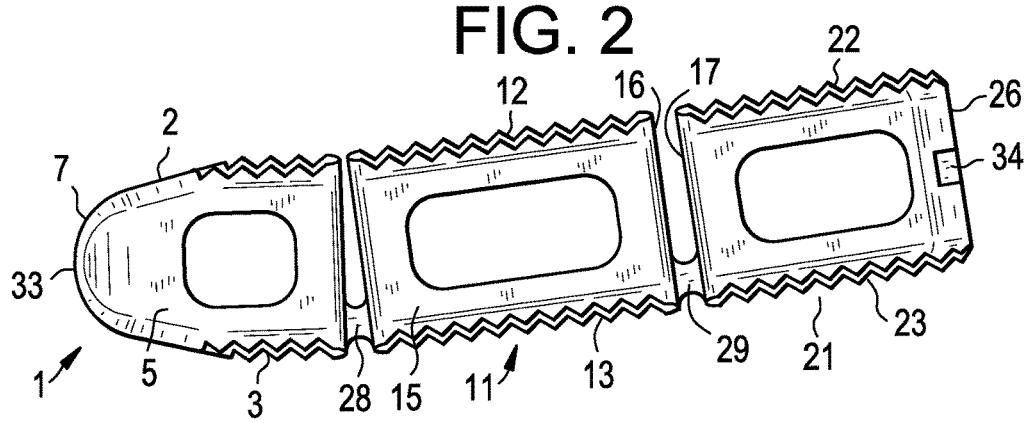
Figure 3:
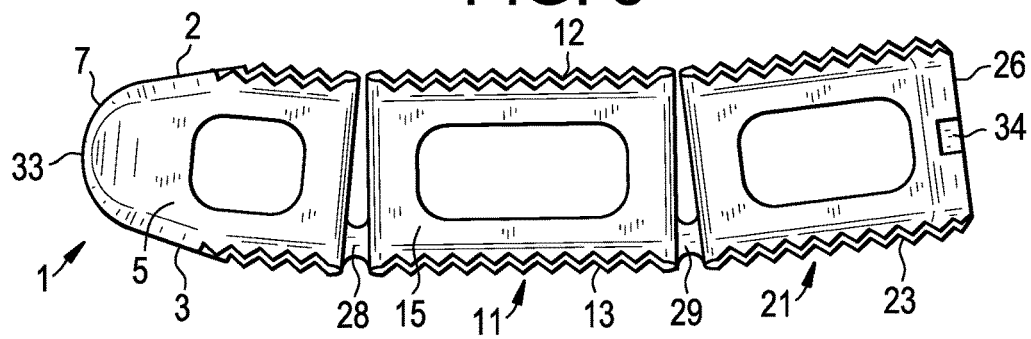
Figure 4:
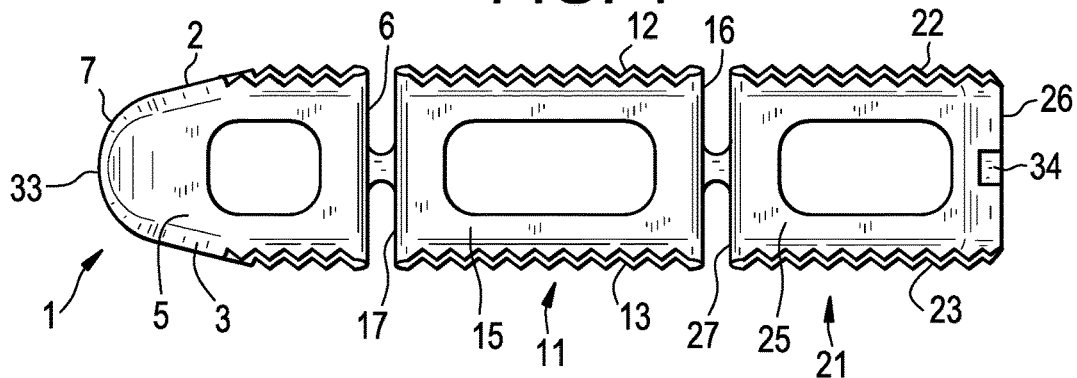
Figure 5:
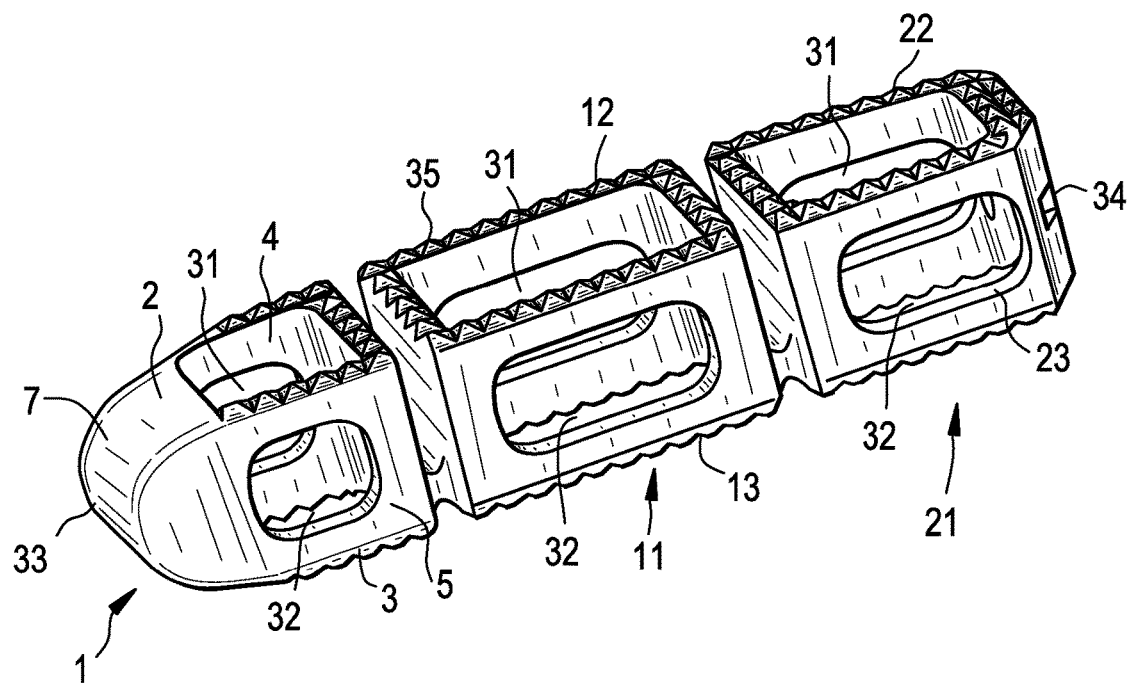

For the purposes of the present invention, insertion or access path that is "substantially in the coronal plane" means insertion +/−30 degrees of an anterior-posterior midline. Preferably, the insertion or access path is between 0 degrees and +30 degrees of the anterior-posterior midline. More preferably, the insertion or access path is between 0 degrees and +15 degrees of the anterior-posterior midline. In some embodiments, the insertion or access path is at about 0 degrees of the anterior-posterior midline.

Now referring to FIGS. 1-8, there is provided a flexible lateral intervertebral fusion device comprising:
 a) a first cage 1 having an upper surface 2, a lower surface 3, anterior 4 and posterior 5 sidewalls therebetween, a proximal wall 6 and a distal wall 7,
 b) a second cage 11 having an upper surface 12, a lower surface 13, anterior 14 and posterior 15 sidewalls therebetween, a proximal wall 16 and a distal wall 17,
 c) a third cage 21 having an upper surface 22, a lower surface 23, anterior 24 and posterior 25 sidewalls therebetween, a proximal wall 26 and a distal wall 27,
wherein the proximal wall of the first cage is integrally attached to the distal wall of the second cage by a first flexible strut 28, and
wherein the proximal wall of the second cage is integrally attached to the distal wall of the third cage by a second flexible strut 29.

In order to promote fusion through the flexible device of the present invention, the walls of the device are commonly provided with throughholes. For example, in FIG. 6, upper and lower surfaces have a through hole 30 running therethrough, while the anterior wall has a throughhole 31 therethrough, and posterior wall has a throughhole 32 therethrough.

In order to promote distraction of the disc space upon entry of the device into the spine, the distal wall of the first cage typically has a bulleted nose 33.

In some embodiments, the proximal wall of the third cage has an attachment feature 34 to allow for threaded attachment to an insertion device.

In order to promote gripping to the opposing vertebral endplates, the upper and lower surfaces of the cages can possess a plurality of teeth 35.

In some embodiments, as in FIG. 1, the flexible strut has a height of no more than 50% of the height defined by the upper and lower bearing surfaces, thereby imparting flexibility to the device in a coronal plane. In some embodiments, the flexible strut has a height of no more than 25% of the height defined by the upper and lower bearing surfaces, thereby imparting flexibility to the device in a coronal plane. In some embodiments, the flexible strut has a reduced height of no more than 10% of the height defined by the upper and lower bearing surfaces, thereby imparting flexibility to the device in a coronal plane.

Figure 6:
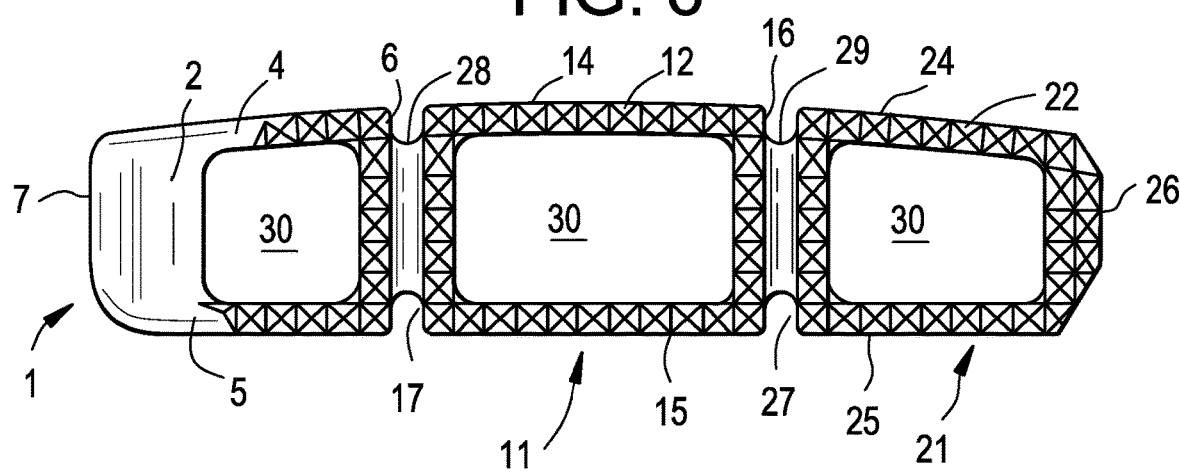
Figure 7:
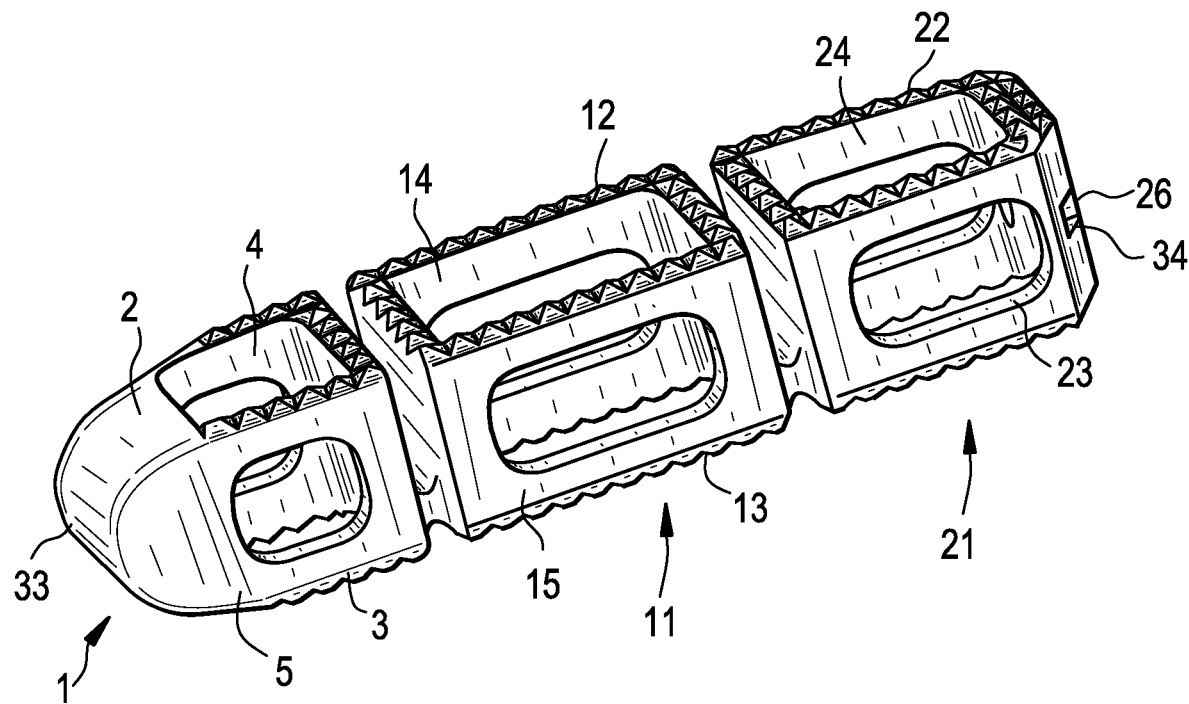
Figure 8:
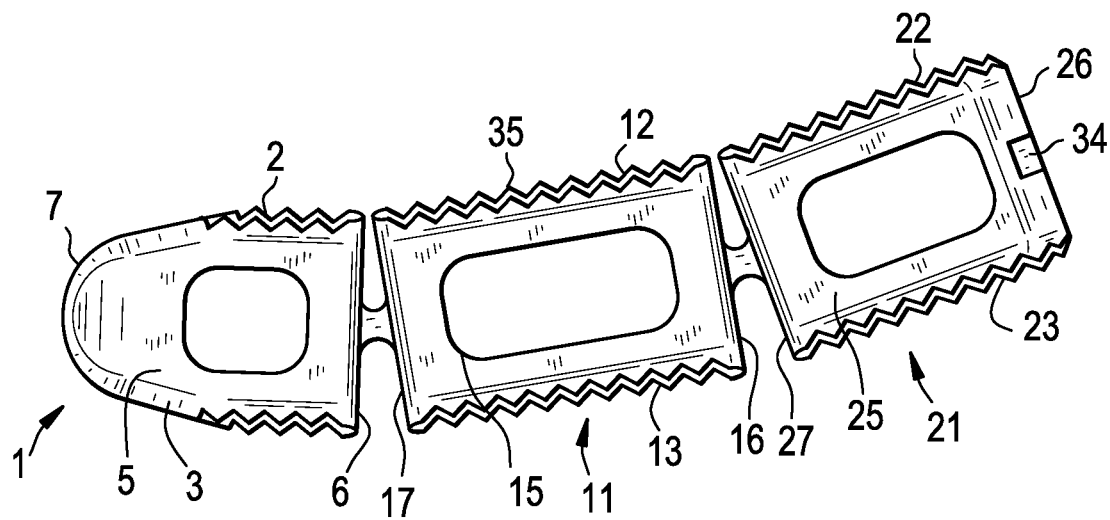

In some embodiments, as in FIG. 6, the flexible strut extends along the anterior—posterior direction of the device, thereby restricting flexibility to the coronal plane.

Now referring to FIGS. 9a-10, there is provided a method of implanting the flexible cage of the present invention.

First, an access portal from the patient's skin to the target disc is prepared, and a disc space is prepared. This can be carried out in accordance with the procedures described in U.S. Ser. No. 61/358,220, filed on Jun. 24, 2010, and entitled "Instruments and Methods for Non-Parallel Disc Space Preparation", and to U.S. Ser. No. 61/379,194, filed on Sep. 1, 2010, and entitled "Flexible Vertebral Body Shavers", the specifications of which are incorporated by reference in their entireties.

Next, the flexible cage of the present invention is inserted into the access portal and carried to the disc space. The flexible cage has a trajectory that is angled with respect to the disc space. As shown in FIG. 9a, as the first cage enters the disc space, the first flexible strut flexes so that the first cage aligns itself to the disc space while the remainder of the cage retains the angled trajectory. Next, upon further advancement into the disc space, as shown in FIG. 9b, as the second cage enters the disc space, the second flexible strut now flexes so that the second cage aligns itself to the disc space while the remaining third cage retains the angled trajectory. Lastly, and now referring to FIG. 9c, the third cage enters the disc space and aligns itself with the opposing endplates.

Although these FIGS. 9a-9c show a single cage flexing at any one time, it is believed that in most real cases, all of the cages will flex to some degree at any one time.

Now referring to FIGS. 11a-11d, 15, 19 and 20, there is provided the linked/jointed device of the present invention, comprising first 51 and second 52 cages, each cage comprising:
  a) an anterior wall 53,54,
  b) a posterior wall 55,56, and
  c) proximal 57,58 and distal 59,60 end walls connecting the anterior and posterior walls,
wherein the proximal end wall of the first cage is connected to the distal end wall of the second cage by a joint 61 that articulates substantially in a plane of the posterior wall.

In some embodiments, the first cage comprises a projection having an articulating surface, while the second cage comprises a recess having a mating articulating surface.

In some embodiments, the proximal end wall of the first cage comprises a projection having an articulating surface and the distal end wall of the second cage comprises a recess having a mating articulating surface.

In some embodiments, the proximal end wall of the first cage comprises a recess 63 having an articulating surface 64, and the distal end wall of the second cage comprises a projection 65 having a mating articulating surface 66.

Figure 11A:
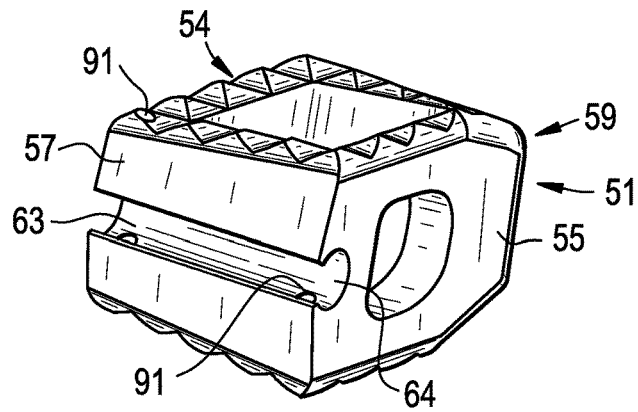
FIGS. 11a-11d, 15, 19 and 20 discloses various views of the cage components of the jointed device of the present invention.
Figure 11B:
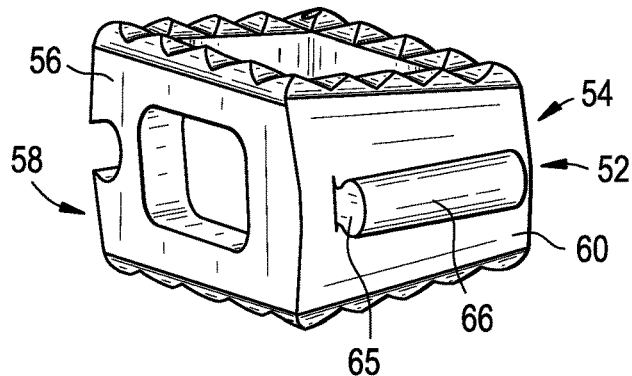
Figure 11C:
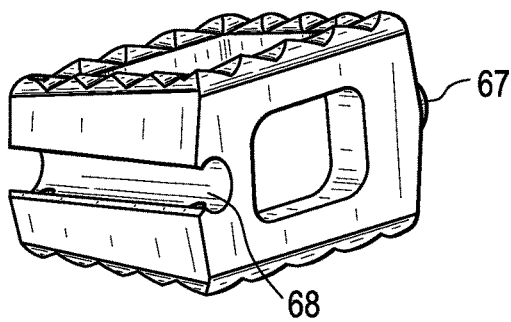
Figure 11D:
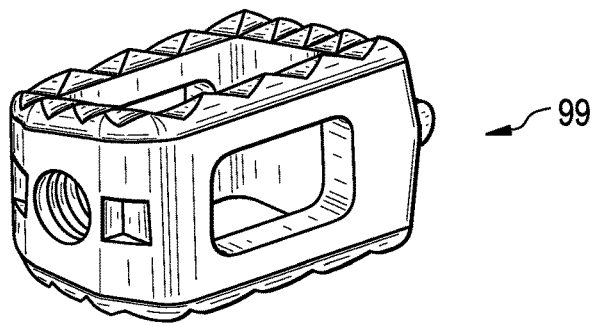
Figure 12:
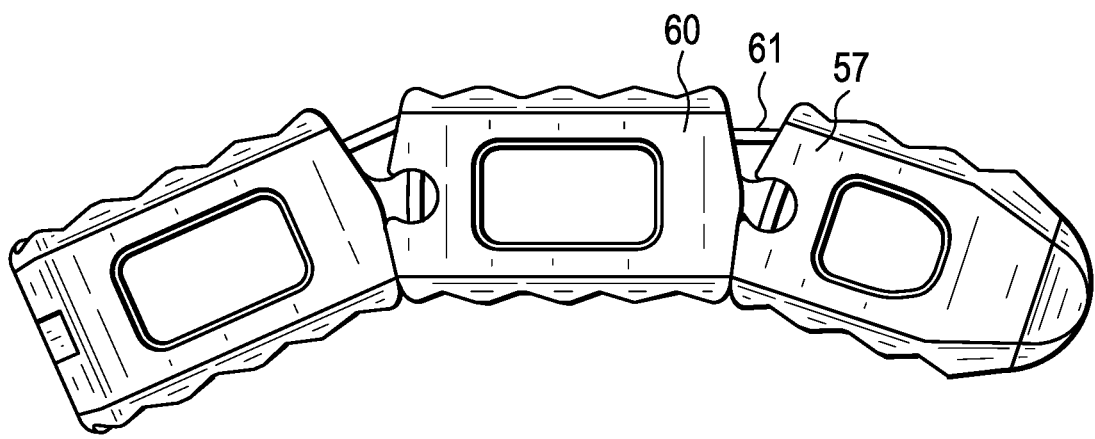
FIGS. 12-14, 16-18 and 21-26 disclose various views of the jointed device of the present invention.
Figure 13:
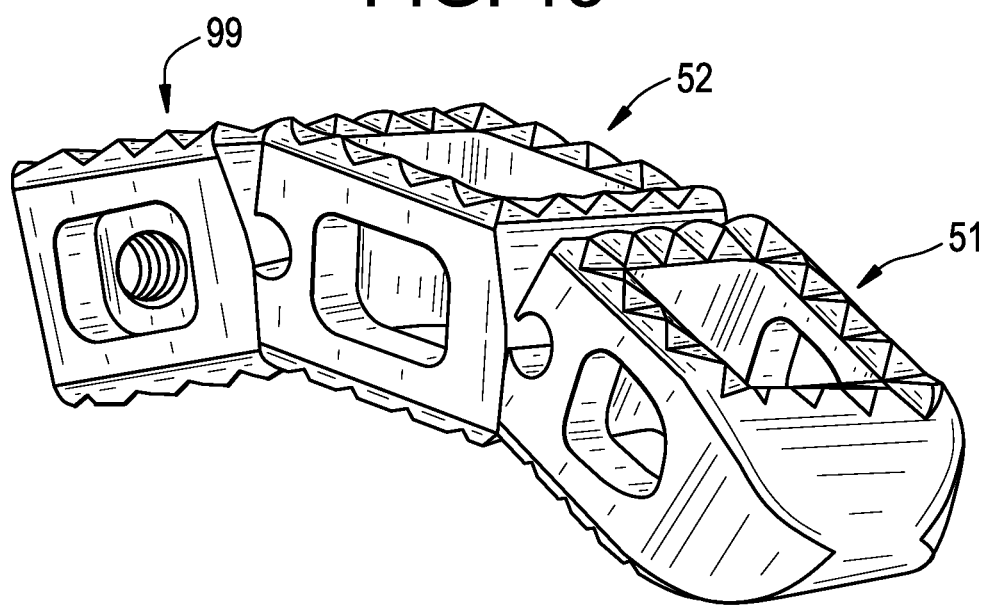

In some embodiments, now referring to FIG. 11c, a cage that is in an intermediate location within the device will have a first joint component 67 (i.e., an articulating projection or recess) on its distal wall for articulating connection to a more distal cage, and a second joint component 68 (i.e., an articulating projection or recess) on its proximal wall for articulating connection to a more proximal cage.

Figure 17:
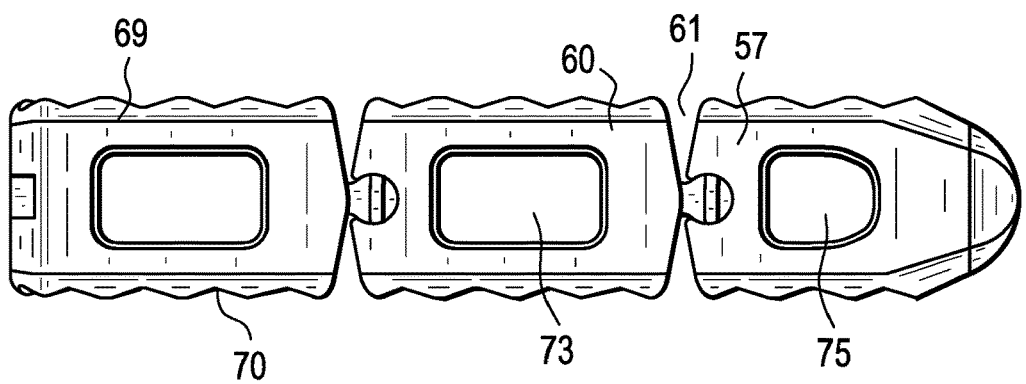
Figure 18:
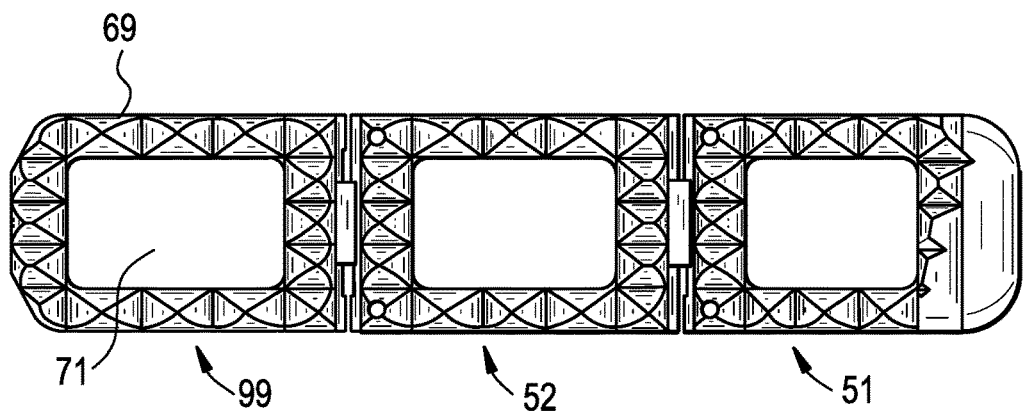
Figure 19:
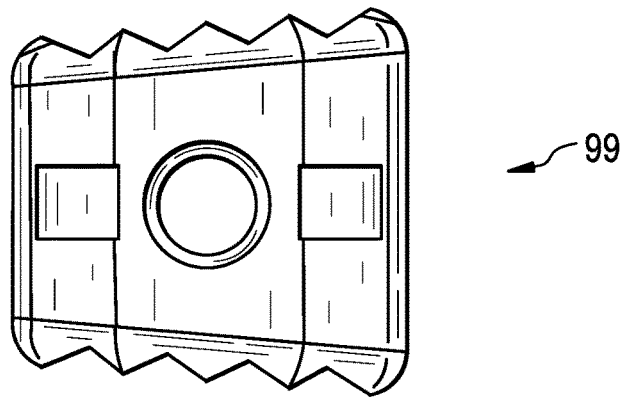
Figure 20:
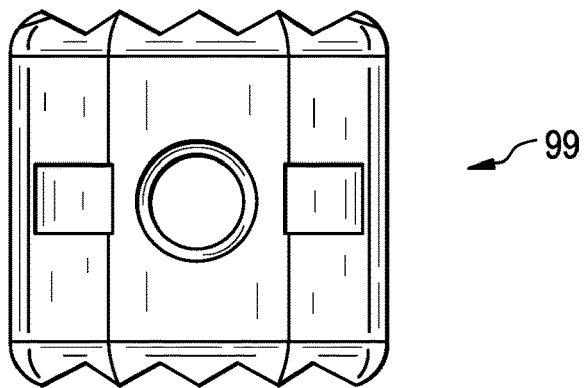

In some embodiments, and now referring to FIGS. 17 and 18, the anterior wall, posterior wall, and proximal and distal end walls form a cage having an upper surface 69, a lower surface 70, and a hole 71 disposed vertically therethrough to promote fusion. In some embodiments, the anterior wall has a hole 73 therethrough to promote fusion. In some embodiments, the posterior wall has a hole 75 therethrough to promote fusion.

Figure 14:
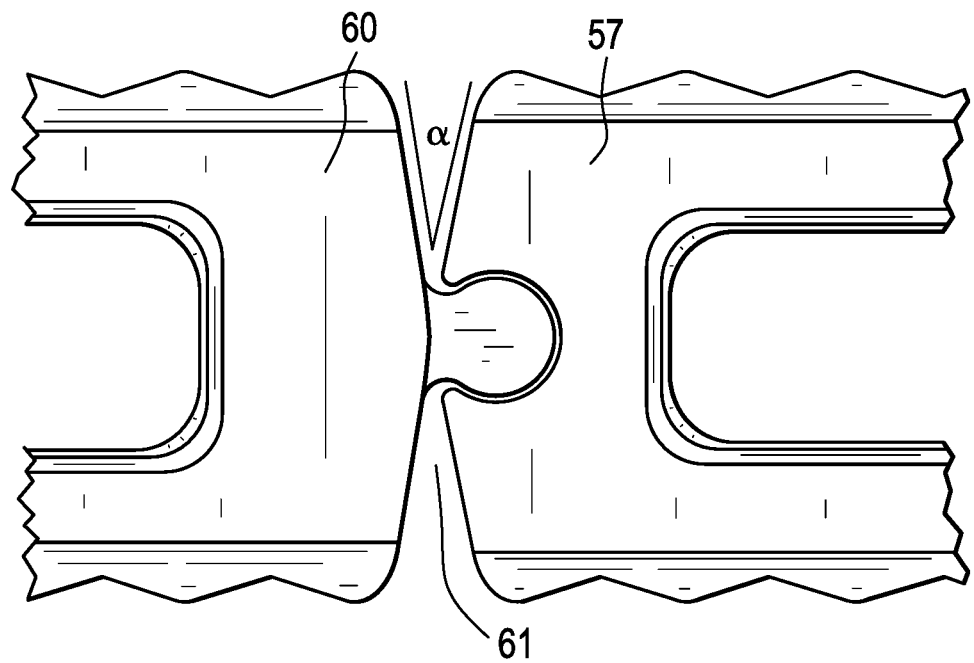

In some embodiments, and now referring to FIG. 14, at least one of the proximal and distal end wall surrounding a joint component forms an acute angle α leading up to the joint component when the projection is normal to the recess. This acute angle allows the joint to articulate over a greater range of motion in comparison to a joint in which the corresponding proximal and distal walls each formed a single plane leading up to the joint component.

Figure 15:
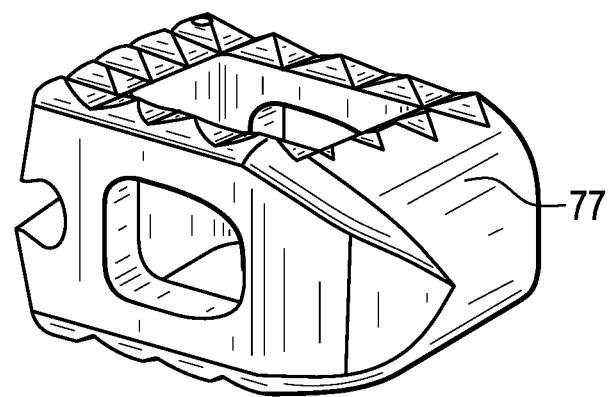

In some embodiments, as in FIG. 15, the first cage is the leading end cage and has a bullet nose 77 on its distal end wall.

Now referring to FIGS. 12-14, 16-18 and 21-26, there is provided a lateral intervertebral fusion device comprising first, second and third cage 99, each cage comprising:
  d) an anterior wall 53,54,81
  e) a posterior wall 55,56,82 and
  f) proximal 57,58,83 and distal 59,60,84 end walls connecting the anterior and posterior walls,
wherein the proximal end wall of the first cage is connected to the distal end wall of the second cage by a first joint 61 that articulates substantially in the coronal plane, and
wherein the proximal end wall of the second cage is connected to the distal end wall of the third cage by a second joint 62 that articulates substantially in the coronal plane.

FIGS. 12-14, 16-18 and 21-26 disclose various views of the jointed device of the present invention.

In other embodiments, the first and third cages each comprise a projection having an articulating surface, while the second cage comprises proximal and distal recesses each having a mating articulating surface.

In some embodiments, there is provided an exploded view of a device in which four cages are sequentially linked by three joints. The lead cage has a bullet nose on its distal end wall and a recess joint component on its proximal end wall. The second cage has a projection joint component on its distal end wall and a recess joint component on its proximal end wall. The third cage has a projection joint component on its distal end wall and a recess joint component on its proximal end wall. The second cage has a projection joint component on its distal end wall and an attachment feature (i.e., a threaded hole) on its proximal end wall.

Figure 21:
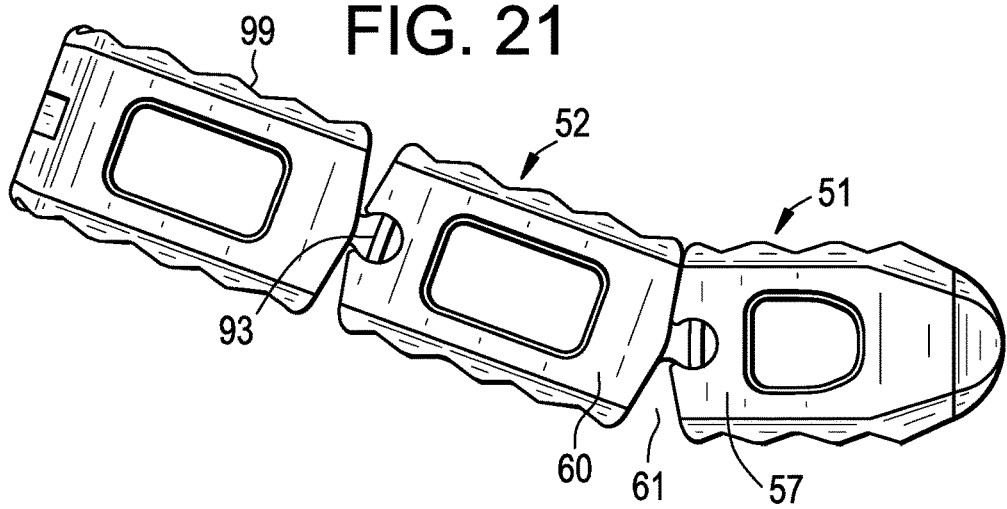
Figure 22:
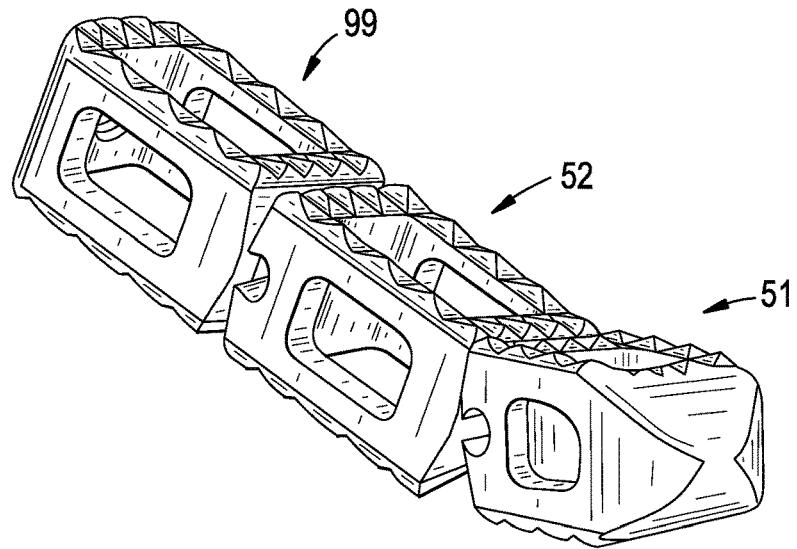
Figure 23:
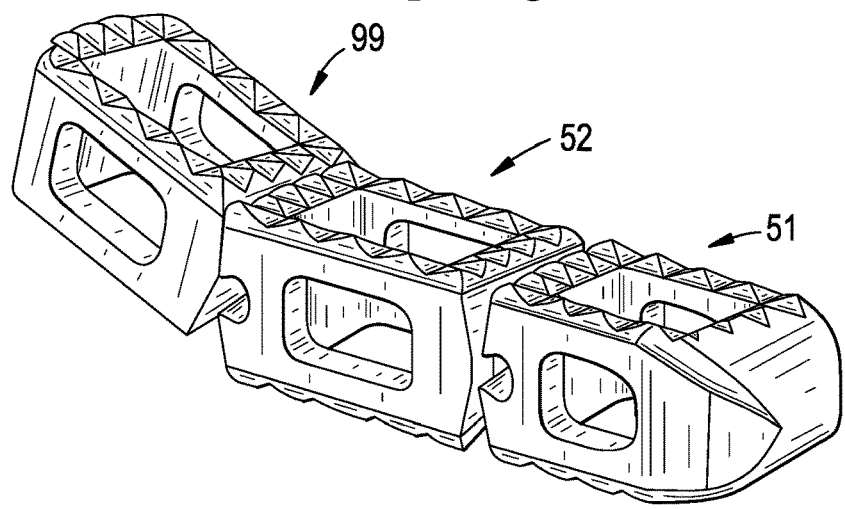
Figure 26:
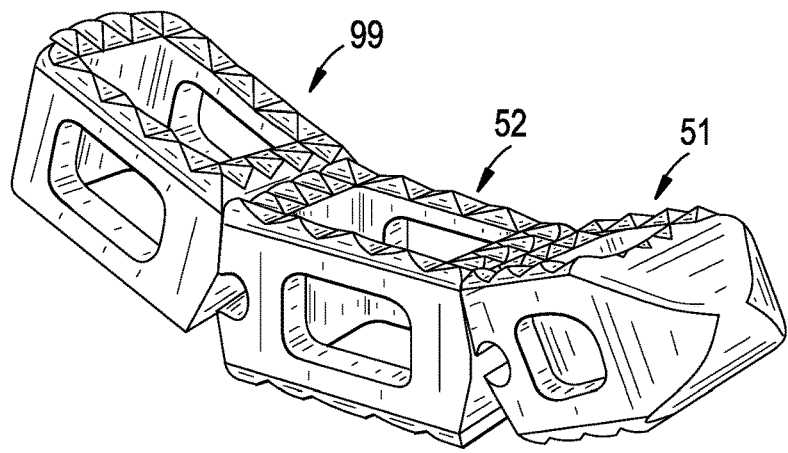
Figure 24:
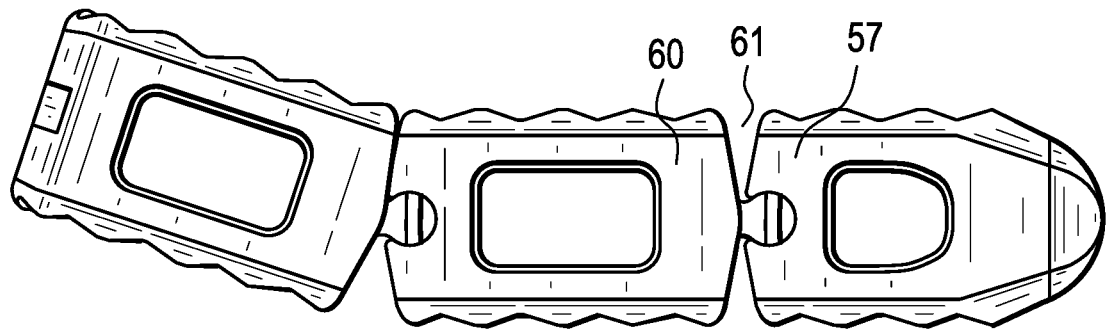
Figure 25:
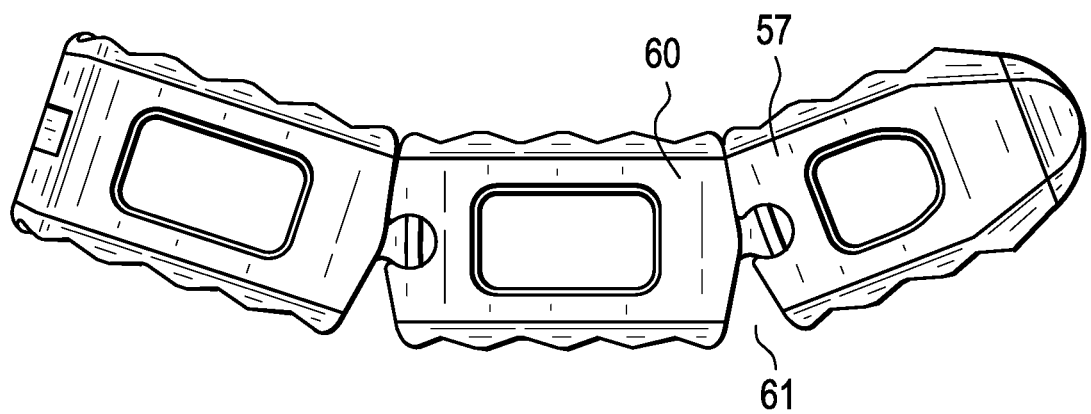
Figure 28A:
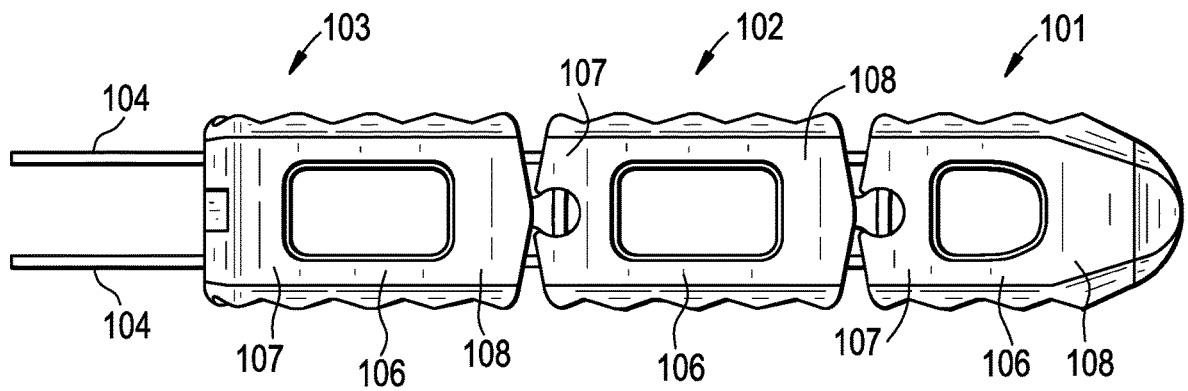
FIGS. 28a-28h disclose various views of a tethered device of the present invention.
Figure 28B:
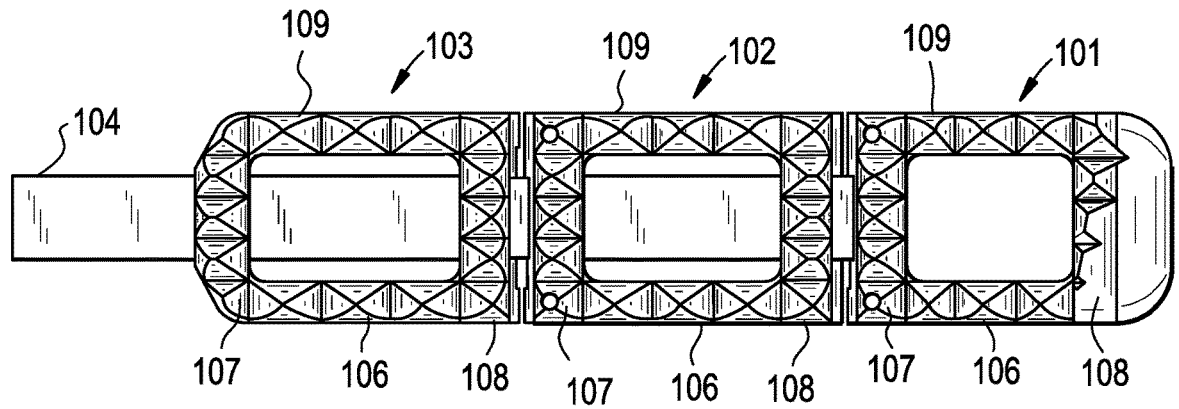
Figure 28C:
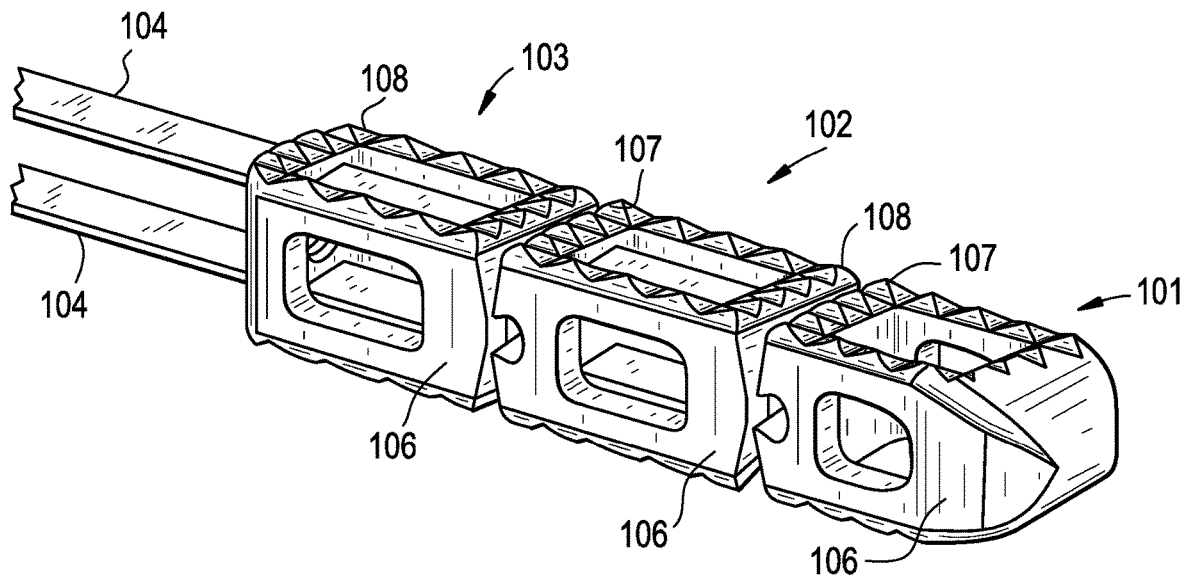
Figure 28D:
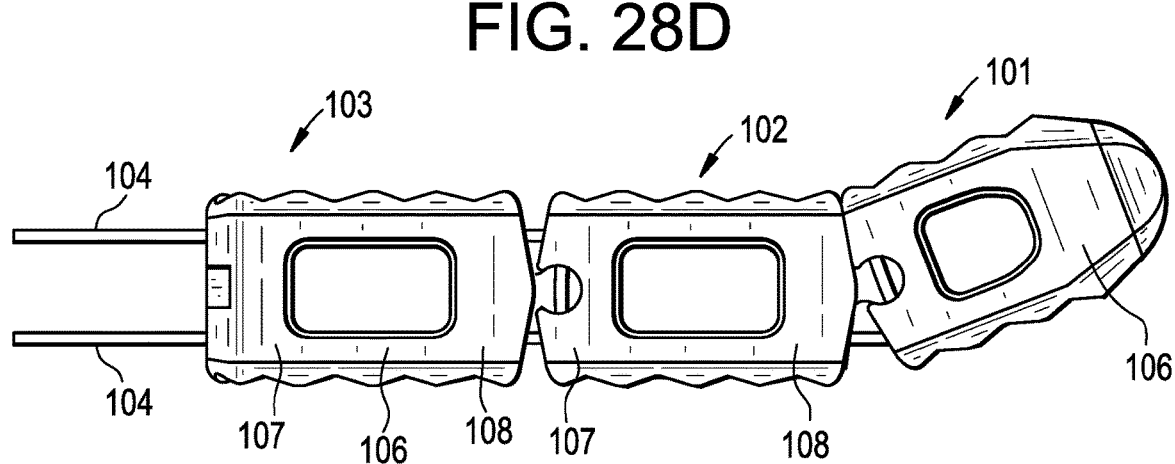
Figure 28E:
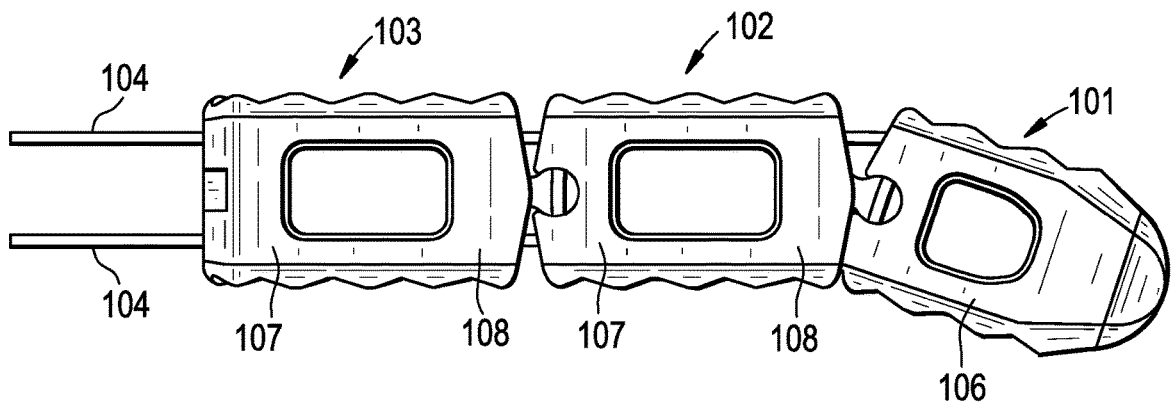
Figure 28F:
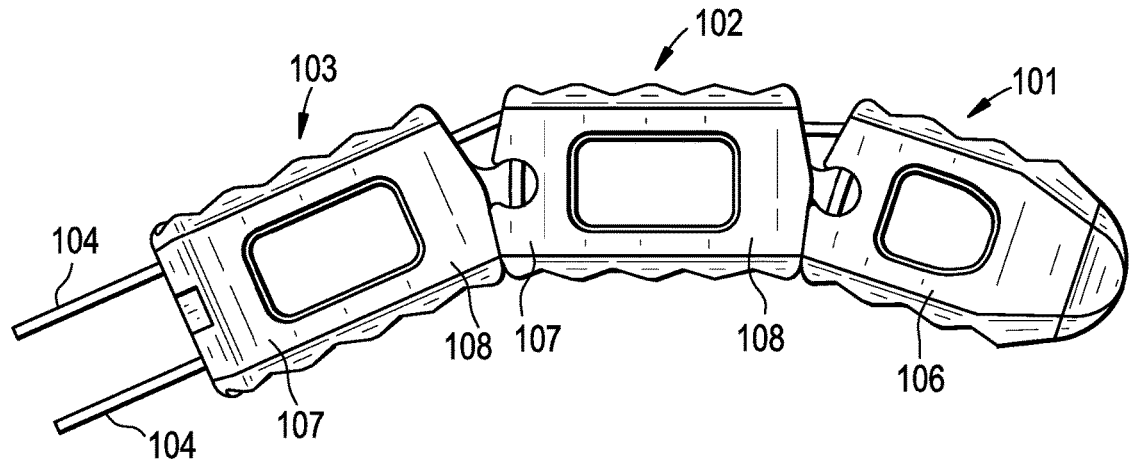
Figure 28G:
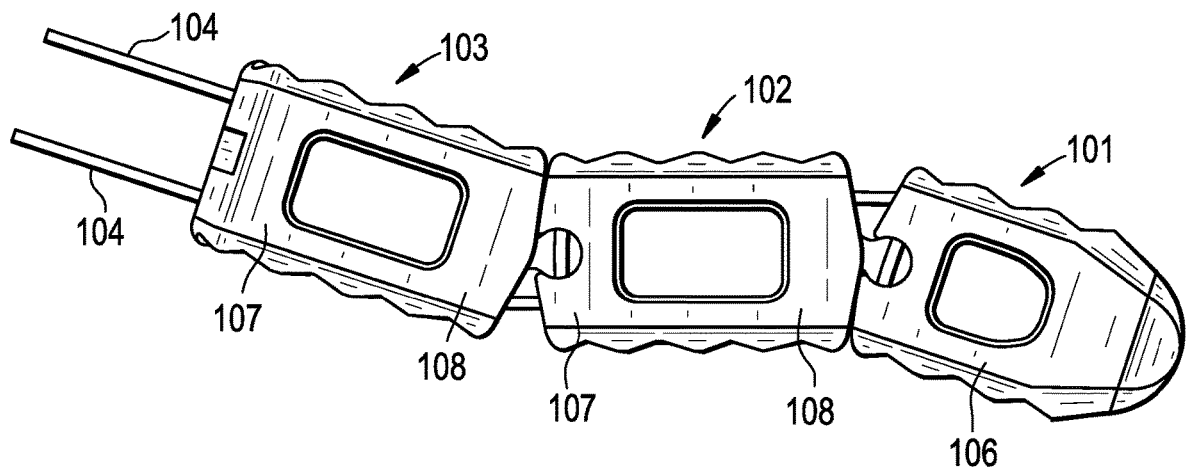
Figure 28H:
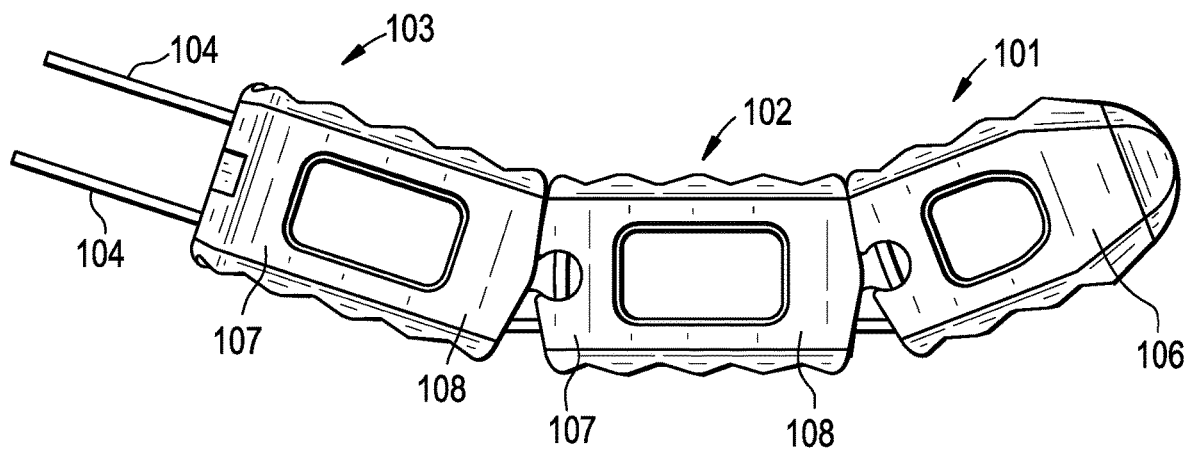

In some embodiments, and now referring to FIGS. 11a and 21, the anterior and posterior wall of the cage that possesses the recess component of the joint may have bilateral vertically disposed through holes 91. These throughholes are sized to accept pins 93. When these pins are bilaterally placed about a joint, they act to keep the projection within the recess. These pins can be made from a radiopaque material to provide for intra-operative imaging. The pins can also be secured by any conventional means, such as press fitting, barbed or threaded means.

Figure 16:
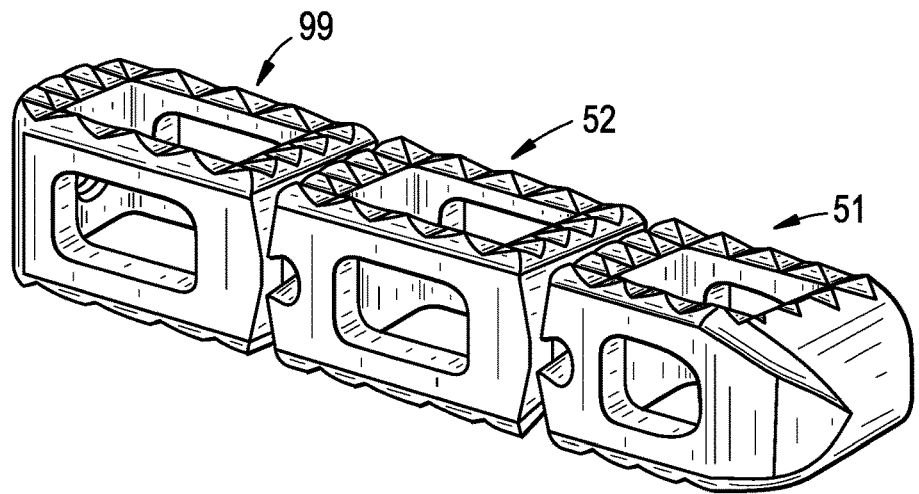

In some embodiments, such as the device shown in FIG. 16, each of the cages within the device has substantially the same height and width. However, in other embodiments, at least one of the cages has a height, width or lordotic angle that is different from that of the remaining cages in the device. Providing such distinct cages allows for intra-operative modularity and assembly to select appropriate segment geometries to maximize contact area at specific locations of the disc/endplate as well as the degree of correction desired. For example, in some cases, the surgeon may select the proximal cage to have an increased width and/or lordosis (as compared to the remainder of the cage train) if the patient's saggital and/or coronal alignments are in need of correction.

In general, the height, width or lordotic angle of the cage be varied across cages within the device. This can be conveniently described as varying the individual silhouettes of the anterior walls of the respective cages within a device.

Therefore, in accordance with the present invention, there is provided a lateral intervertebral fusion device comprising first and second cages, each cage comprising:

a) an anterior wall having a silhouette,
b) a posterior wall having a height and a width, and
c) proximal and distal end walls connecting the anterior and posterior walls, wherein the proximal end wall of the first cage is connected to the distal end wall of the second cage by a joint that articulates substantially in a plane of the posterior wall, wherein the silhouette of the anterior wall of the first cage is different from the silhouette of the anterior wall of the second cage.

The intent of providing an articulation within the device is to achieve articulation within the coronal plane so as to allow vertical bending of the device during its angled, lateral insertion. Therefore, in some embodiments, there is provided a method comprising the step of inserting into a disc space a lateral intervertebral fusion device comprising first and second cages, each cage comprising:
a) an anterior wall,
b) a posterior wall,
c) proximal and distal end walls connecting the anterior and posterior walls wherein the proximal end wall of the first cage is connected to the distal end wall of the second cage by a joint, wherein the device is oriented such that the joint articulates substantially in the coronal plane.

In use, the jointed device of the present invention is made by first selecting the appropriate cages desired in the device. Next, the surgeon laterally slides the projection component of a first cage into the recess of its mating cage. Next, the surgeon secures the joint by placing the pins in the vertical throughholes located in the wall forming the recess of the mating cage. This assembly process is repeated until the desired device is constructed.

The device so constructed is then used in a manner substantially similar to the flexible cage discussed above, as shown in FIG. 27.

Now referring to FIGS. 28*a-h*, there is provided an intervertebral fusion device comprising first 101, second 102 and third 103 cages and a flexible band 104, wherein each cage comprises:
a) an anterior wall 109,
b) a posterior wall 106,
c) proximal 107 and distal 108 end walls connecting the anterior and posterior walls, and wherein the flexible band runs from proximal end wall of the first cage, through the second cage and to the distal end of the third cage.

Preferably, the flexible band can be pre-tensioned, thereby providing a controlled amount of stiffness of the construct's flexibility.

Figure 29:
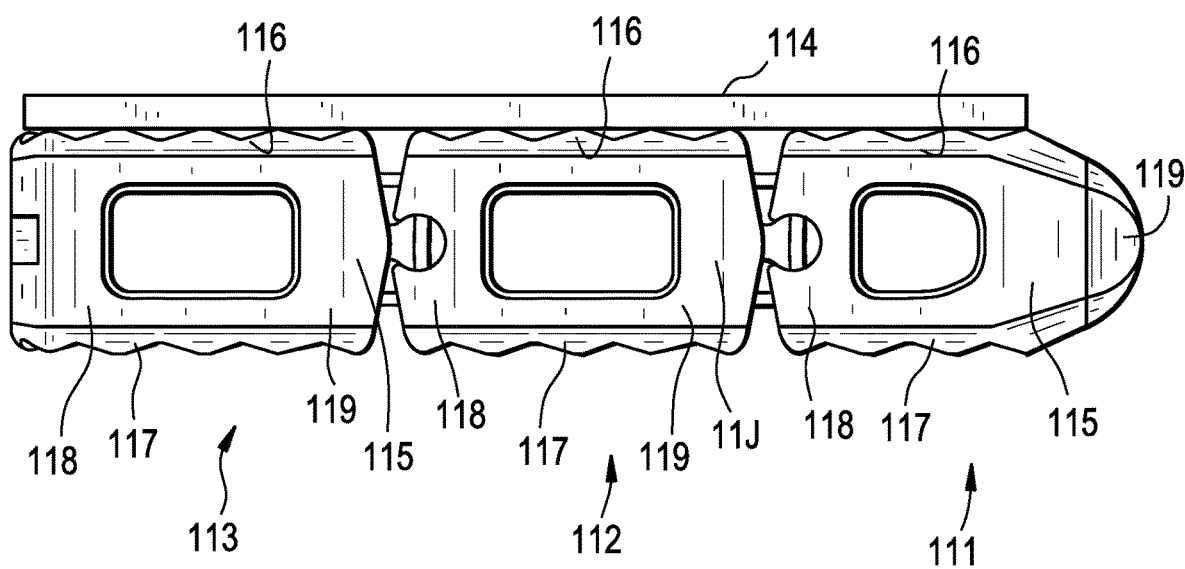
FIG. 29 discloses an adhesive-coupled device of the present invention.

Now referring to FIG. 29, there is provided a lateral intervertebral fusion device comprising first 111, second 112 and third 113 cages and an adhesive tape 114, wherein each cage comprises:
a) an anterior wall having an upper surface and a lower surface,
b) a posterior wall 115 having an upper surface 116 and a lower surface 117,
c) proximal 118 and distal 119 end walls connecting the anterior and posterior walls,
and wherein the adhesive tape is adhered to the cages along the upper surface of the proximal end wall of the first cage, across the second cage and to the upper surface distal end of the third cage.

In an alternate tape embodiments, there is provided a lateral intervertebral fusion device comprising first, second and third cages and an adhesive tape, wherein each cage comprises:
d) an anterior wall having an upper surface and a lower surface,
e) a posterior wall having an upper surface and a lower surface,
f) proximal and distal end walls connecting the anterior and posterior walls,
and wherein the adhesive tape is adhered to the cages along the lower surface of the proximal end wall of the first cage, across the second cage and to the lower surface distal end of the third cage.

Figure 30:
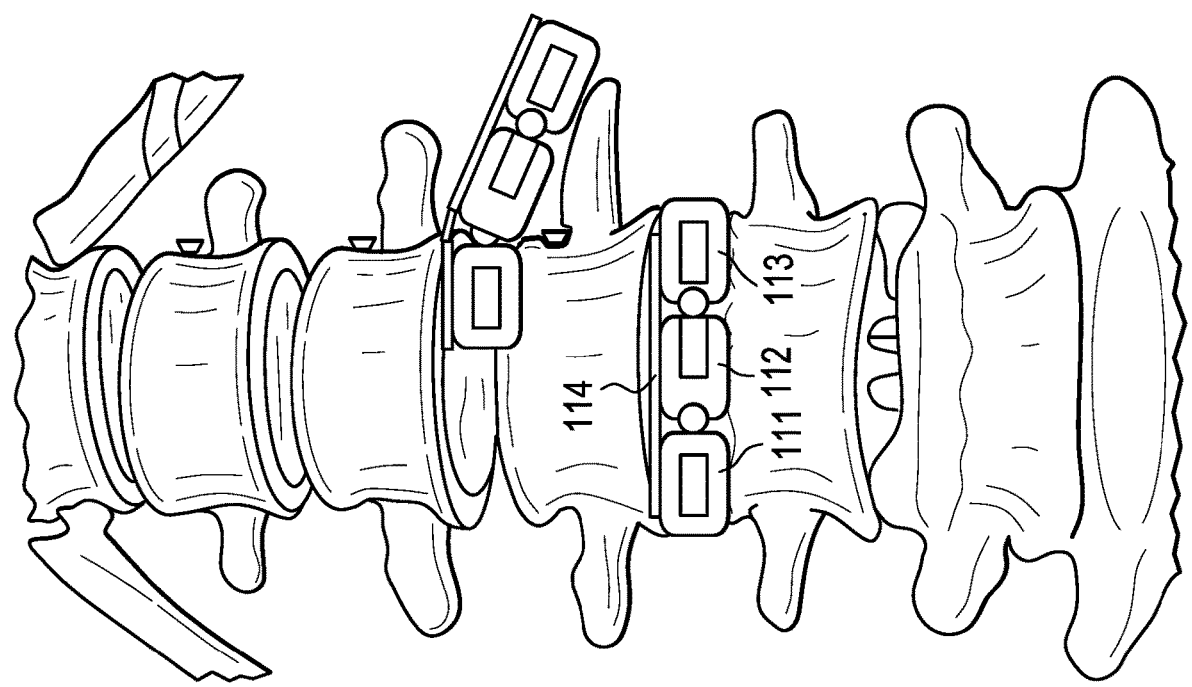
FIG. 30 discloses a method of implanting a tethered device of the present invention.
Figure 31:
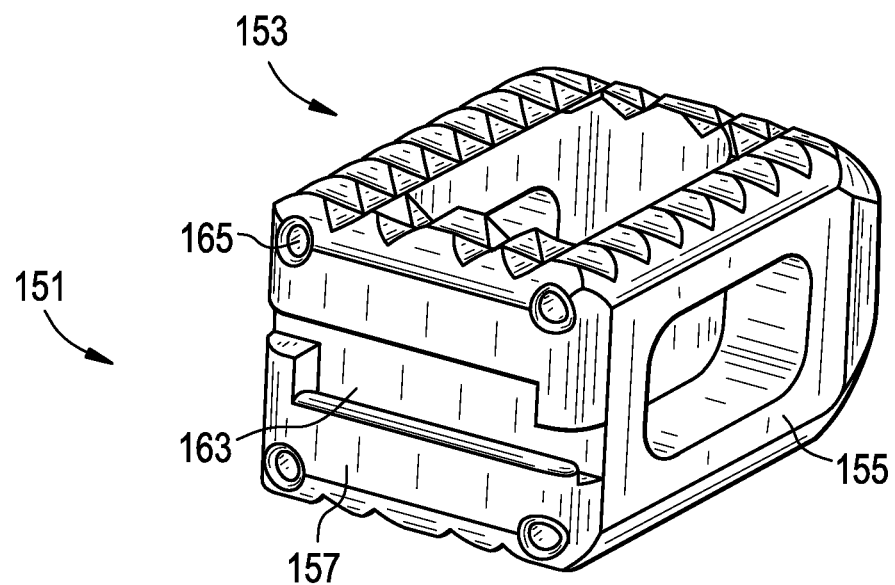
FIGS. 31-34 disclose various views of components of a snap device of the present invention.
Figure 32:
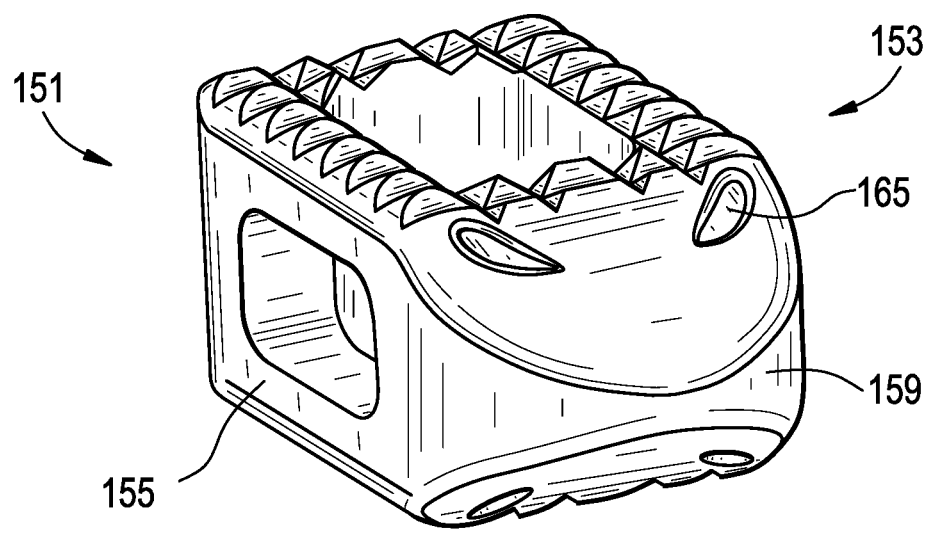
Figure 33:
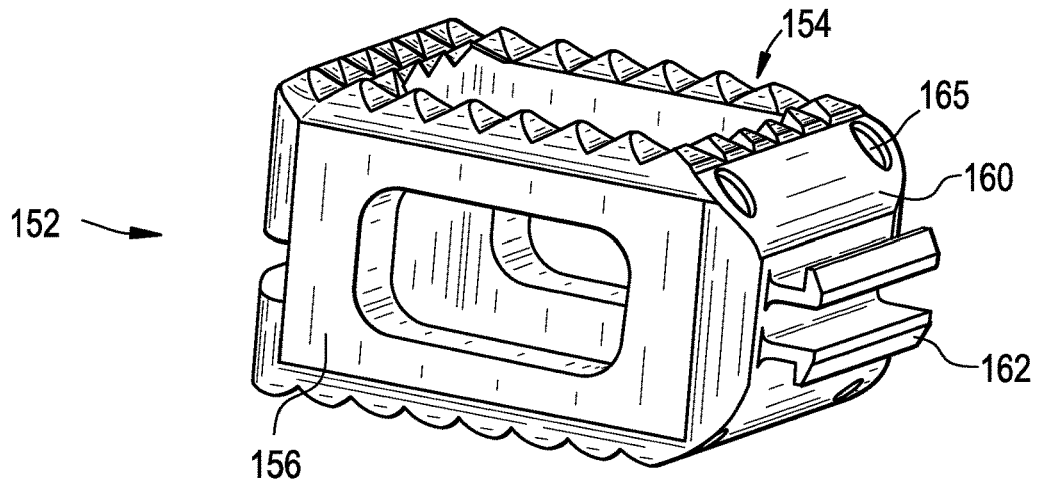
Figure 34:
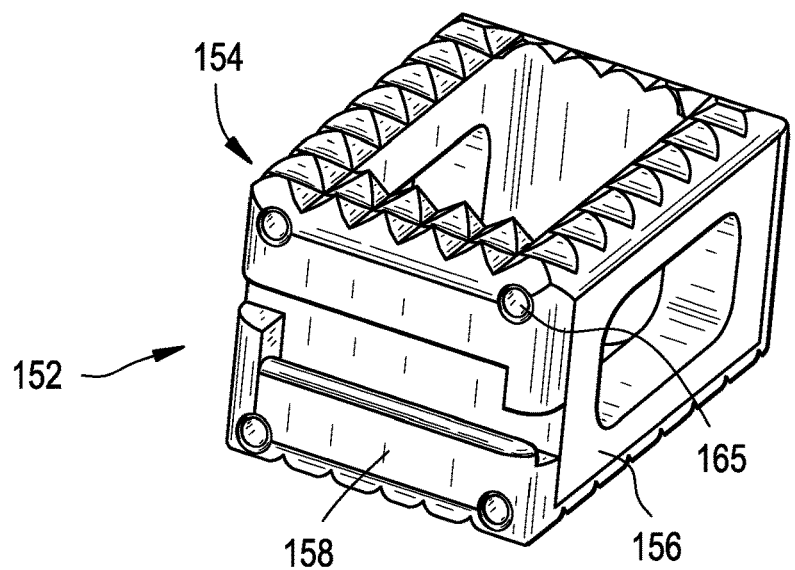
Figure 35:
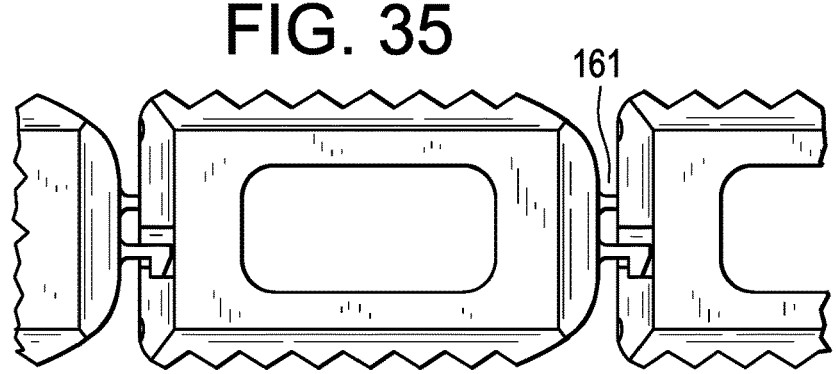
FIGS. 35 and 37 discloses a various views of the snap device of the present invention.
Figure 36A:
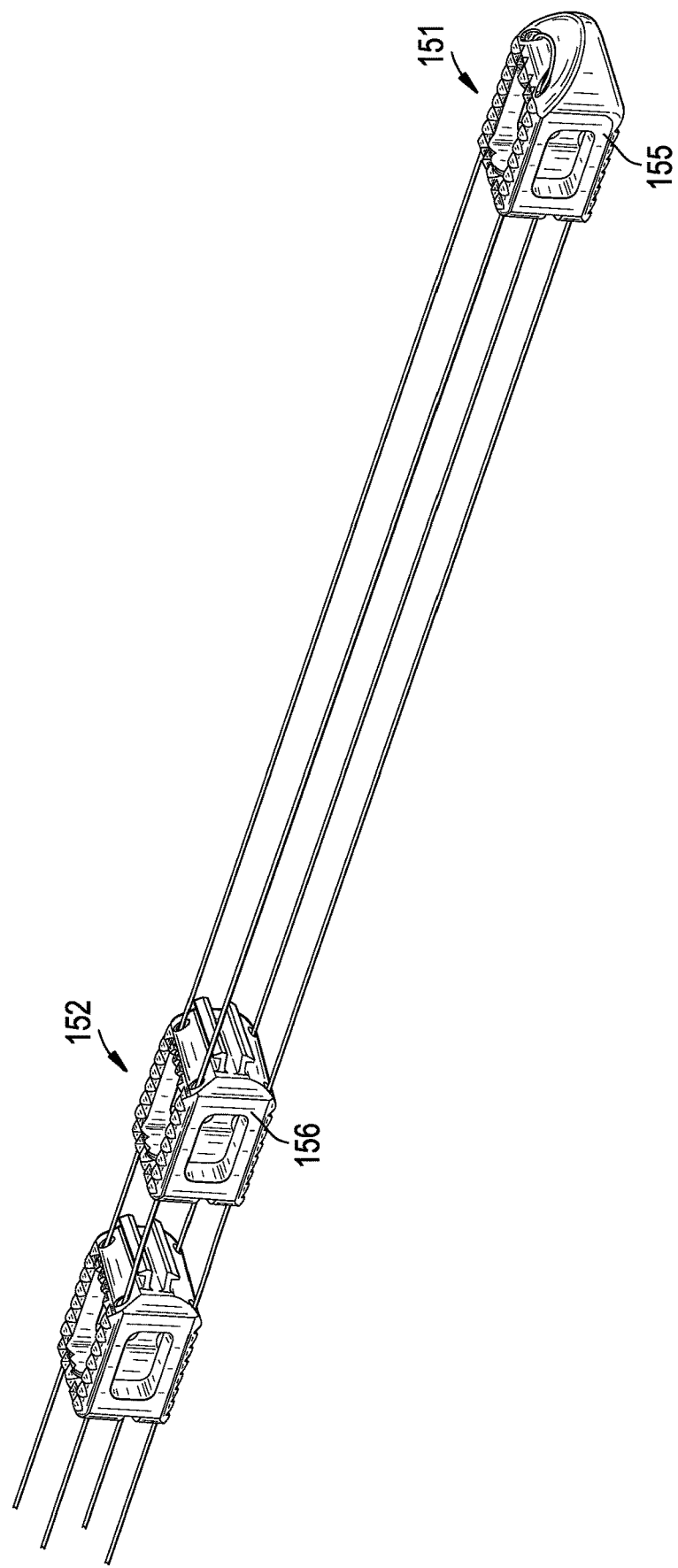
Figure 36D:
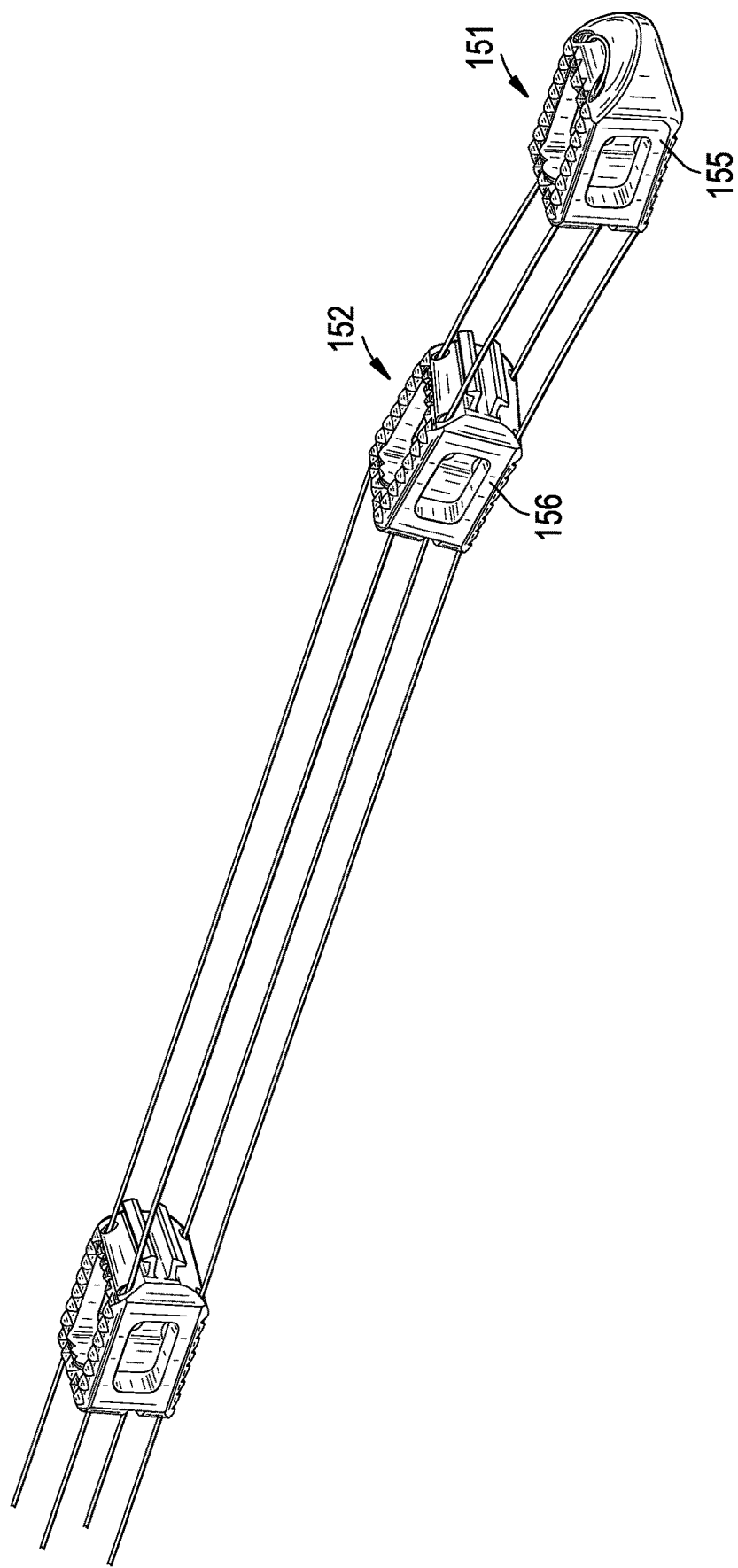
Figure 36E:
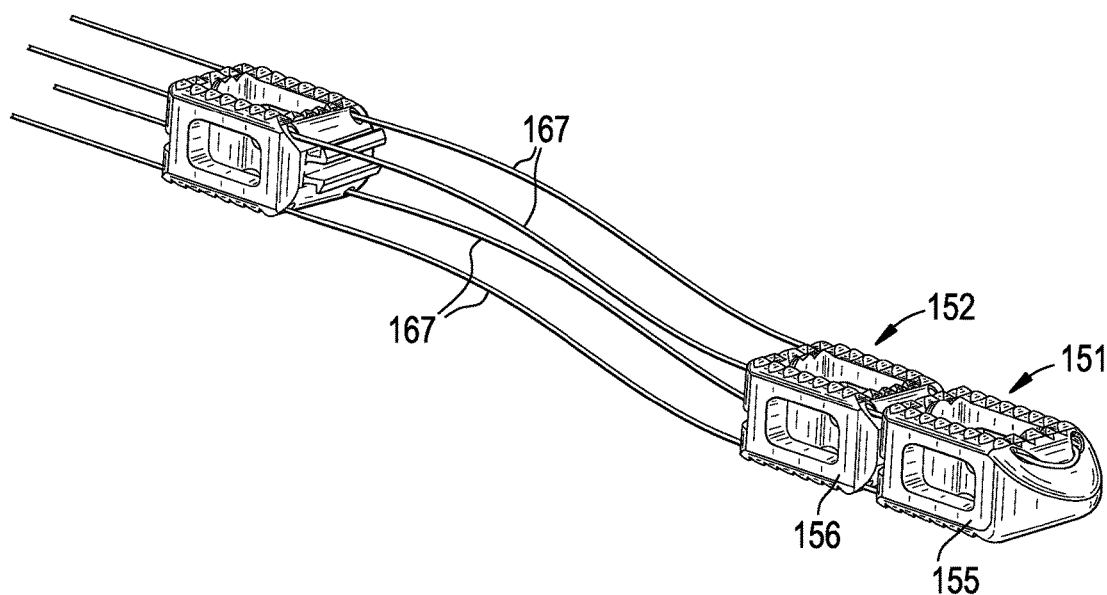
Figure 36F:
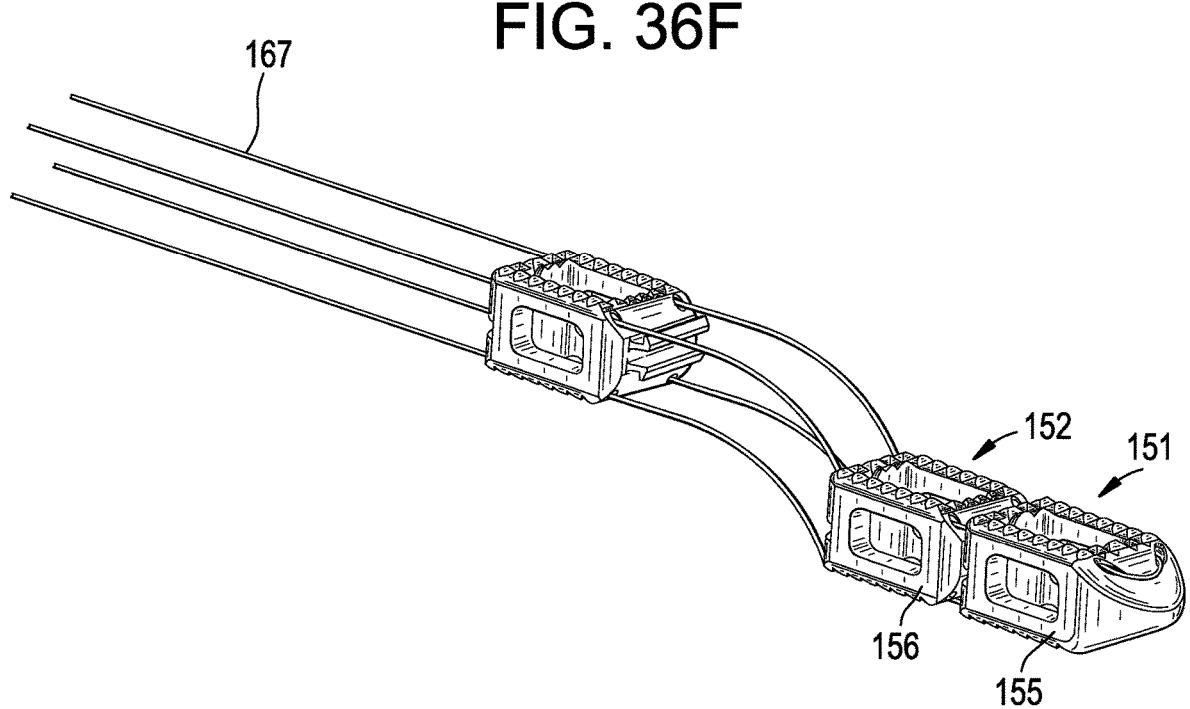
Figure 36G:
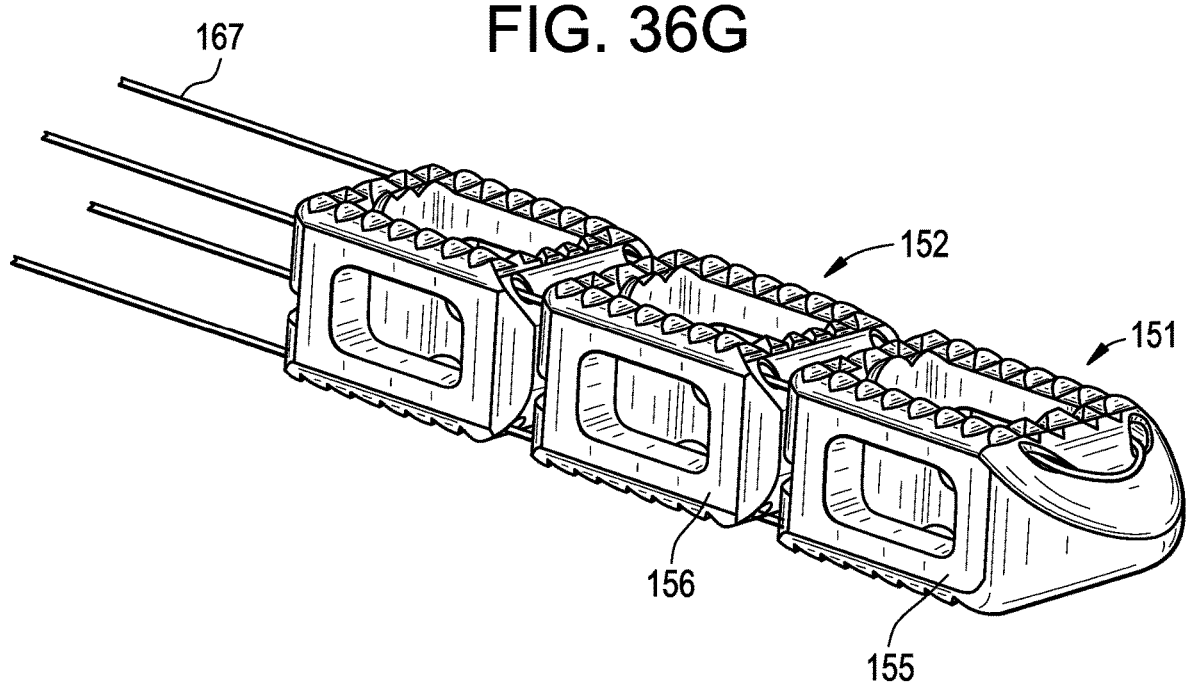
Figure 37:
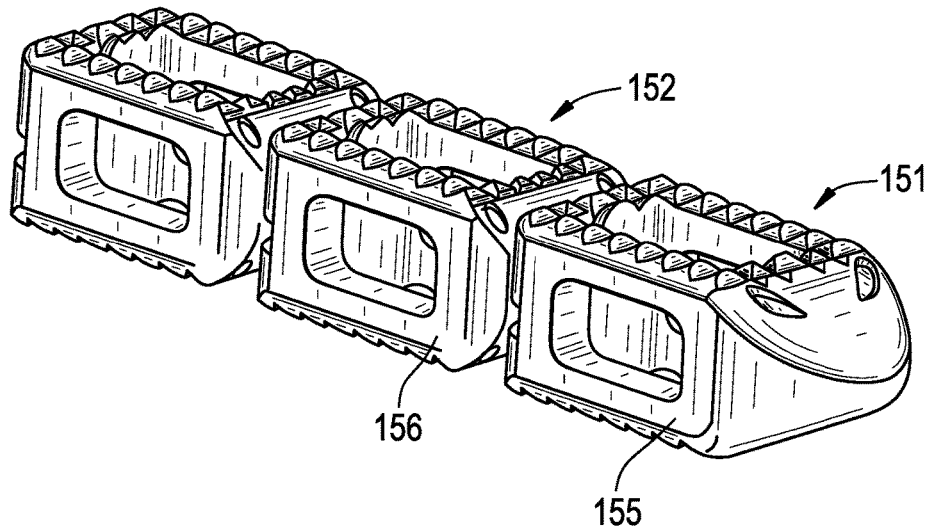

The device so constructed is then used in a manner substantially similar to the flexible cage discussed above, as shown in FIG. 30.

In some embodiments, the cages are individually and sequentially introduced into the disc space. Once in the disc space, they are connected to each other by an interconnection means (such as a snap-fit connection) located on their proximal and distal end walls.

Now referring to FIGS. 31-35, and 37 there is provided the snap cage of the present invention, comprising a lateral intervertebral fusion device comprising first 151 and second 152 cages and a tether 167, each cage comprising:
a) an anterior wall 153,154,
b) a posterior wall 155,156, and
c) proximal 157,158 and distal 159,160 end walls connecting the anterior and posterior walls,
wherein the proximal end wall of the first cage is fixedly secured to the distal end wall of the second cage by a securement means 161,
wherein each cage has at least one hole 165 passing therethrough, and the tether is received through at least one hole in each cage.

In some embodiments, the securement means is a snap-connection 161. In some embodiments, the snap-connection comprises a male component 162 and a female component 163.

In some embodiments, there are at least two tethers that pass through two sets of holes to provide delivery guidance to the cages.

In using the snap cage of the present invention, and now referring to FIGS. 36*a-g*, the cages are individually and sequentially introduced into the disc space by sequentially traveling down the set of tethers. Once in the disc space, they are connected to each other by snap-fitting their securement components located on their proximal and distal end walls.

Therefore, in accordance with the present invention, there is provided a method of implanting an intervertebral fusion device in a disc space in a patient, comprising the steps of:
a) creating an access path to the disc space wherein the access path lies substantially in a coronal plane;
b) advancing a tether through the access path and into the disc space;
c) advancing a first cage over the tether and into the disc space,
d) advancing a second cage over the tether and into the disc space, and.
e) attaching the second cage to the first cage within the disc space to assemble the intervertebral fusion device,
wherein the first and second cages remain over the tether during the attachment step.

The cages of the present invention may be made from any non-resorbable material appropriate for human surgical implantation, including but not limited to, surgically appropriate metals, and non-metallic materials, such as carbon fiber composites, polymers and ceramics.

The interbody devices are preferably made out of PEEK or CFRP or any other suitable material providing adequate strength and radiolucency. However, implantable metals such as titanium or stainless steel components may be required to ensure adequate strength for either the interbody device. In some cases the interbody device can be made as a combination of PEEK and metal. In some cases, resorbable materials such as polylactide, polyglycolide, and magnesium are preferred.

In some embodiments, the cage material is selected from the group consisting of PEEK, ceramic and metallic. The cage material is preferably selected from the group consisting of metal and composite (such as PEEK/carbon fiber).

If a metal is chosen as the material of construction for a component, then the metal is preferably selected from the group consisting of titanium, titanium alloys (such as Ti-6Al-4V), chrome alloys (such as CrCo or Cr—Co—Mo) and stainless steel.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; polyphenylene and mixtures thereof.

If a ceramic is chosen as the material of construction for a component, then the ceramic is preferably selected from the group consisting of alumina, zirconia and mixtures thereof. It is preferred to select an alumina-zirconia ceramic, such as BIOLOX Delta™, available from CeramTec of Plochingen, Germany. Depending on the material chosen, a smooth surface coating may be provided thereon to improve performance and reduce particulate wear debris.

In some embodiments, the cage member comprises PEEK. In others, it is a ceramic.

In some embodiments, the first component consists essentially of a metallic material, preferably a titanium alloy or a chrome-cobalt alloy.

In some embodiments, the components are made of a stainless steel alloy, preferably BioDur® CCM Plus® Alloy available from Carpenter Specialty Alloys, Carpenter Technology Corporation of Wyomissing, Pa. In some embodiments, the outer surfaces of the components are coated with a sintered beadcoating, preferably Porocoat, available from DePuy Orthopaedics of Warsaw, Ind.

In some embodiments, the components are made from a composite comprising carbon fiber. Composites comprising carbon fiber are advantageous in that they typically have a strength and stiffness that is superior to neat polymer materials such as a polyarylethyl ketone PAEK. In some embodiments, each component is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
a) 40-99% (more preferably, 60-80 vol %) polyarylethyl ketone (PAEK), and
b) 1-60% (more preferably, 20-40 vol %) carbon fiber,
wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

Although the present invention has been described with reference to its preferred embodiments, those skillful in the art will recognize changes that may be made in form and structure which do not depart from the spirit of the invention.

In other embodiments, the components are made from resorbable materials, such as Biocryl Rapide™, a PLA, PLG, TCP composite marketed by DePuy Mitek, located in Raynham, Mass.

When resorbable materials are selected, Preferred bioresorbable materials which can be used to make the sutures of the present invention include bioresorbable polymers or copolymers, preferably selected from the group consisting of hydroxy acids, (particularly lactic acids and glycolic acids; caprolactone; hydroxybutyrate; dioxanone; orthoesters; orthocarbonates; and aminocarbonates). Preferred bioresorbable materials also include natural materials such as chitosan, collagen, cellulose, fibrin, hyaluronic acid; fibronectin, and mixtures thereof. However, synthetic bioresorbable materials are preferred because they can be manufactured under process specifications which insure repeatable properties.

A variety of bioabsorbable polymers can be used to make the suture of the present invention. Examples of suitable biocompatible, bioabsorbable polymers include but are not limited to polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-,L- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, χ,χ-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonates), for the purpose of this invention, are understood to include those polymers as described by Kemnitzer and Kohn, in the *Handbook of*

*Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer-based polymers made from L-lactide, D,L-lactide, lactic acid, glycolide, glycolic acid, para-dioxanone, trimethylene carbonate and ε-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al, Hardwood Academic Press, pp. 161-182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99-118 (1997).

In another embodiment, there is provided an intervertebral fusion device having multiple cage components inserted into the disc space via a guide wire, wherein the cage components are inserted either sequentially or together as an assembly. The first (distal) cage component possesses a bulleted feature (e.g., either a substantially wedged or substantially conical shape) on the leading (distal) face for distraction of the vertebral endplates, and an opening in at least its proximal faces. This cage is fed with a wire (such as a K-wire, cable, tether, or braid) into the disc space, whereby the wire is received in the opening(s) of the cage component. The wire and cage may be assembled just prior to surgery, or they may be pre-assembled, such as through manufacturing methods that use molds, threaded anchors, mechanical interlocks, or adhesives.

An optional intermediate cage component may also be used. It has openings (as throughholes) in its proximal and distal end faces, wherein the throughholes are likewise able to receive and pass the wire.

The opening of either cage component may be a hole in the proximal or distal end faces that allows an end of the wire to be inserted through the component. In other embodiments, the opening may be a slot that allows the cage component to be assembled with the wire from a slot in a side wall (i.e., anterior wall or posterior wall) of the cage component.

This embodiment further comprises a final cage component, wherein the final cage component has an opening in each of its distal and proximal faces for receiving the wire and a mating feature adapted to secure the wire to the final cage component. This mating feature, which is located proximal to the proximal face of this final component, may be a clamp, plug, threaded device, or other mechanical interlock.

The opposing faces of adjacent cage components may be fixedly joined together after insertion via locking means. Some exemplary locking means may include a snap-fit, a taper lock, and other mechanical interlock features that promote rigidity in the assembled device. Alternatively, the assembly may possess articulating interconnections at the interfaces by using joint-making shapes, such as a ball-and-socket joint or a cylinder-and-groove joint, to promote articulation of the device.

The wire may be disengaged from the cage components upon completion of cage insertion. This may be accomplished by turning and removing the entire wire (if the wire is secured by a threaded connection), or by severing the portion of the wire extending proximally from the final cage component.

Also in accordance with the present invention is a surgical instrument for advancing a cage component on a wire, the instrument comprising:
  i) a cannulated sleeve extending from the discectomy site to the outside of the patient's body and adapted to receive the wire passing through a first cage component, the sleeve having a distal end portion and a proximal end portion, and
  ii) a compression component threadably received on the proximal end portion of the sleeve and adapted to provide:
    a) fixation to the wire at a location proximal of the sleeve, and
    b) expansion between the fixation location and the sleeve, used to tension the wire and compress the sleeve as it abuts either the cage or an intermediate feature mating the sleeve to the cage, thus assisting in insertion and positional adjustments of the cage components.

In some embodiments, the cages are individually and sequentially introduced into the disc space via a guide wire connected to the first cage. Once in the disc space, they may be connected to each other by, for example, a snap-fit connection located on their proximal and distal end walls.

Therefore, in accordance with the present invention, there is provided (claim 47) an assembly comprising i) an intervertebral fusion device comprising first and second fusion cages and ii) a wire, each fusion cage comprising:
a) an anterior wall,
b) a posterior wall, and
c) proximal and distal end walls connecting the anterior and posterior walls,
wherein each fusion cage has at least one opening passing at least partially through either its distal or proximal end wall, and
wherein the wire passes through the at least one opening in each cage.

In some embodiments, the cages are secured together through connectors such as a snap-connection 161. In some embodiments, the snap-connection comprises a male component 162 and a female component 163.

Figure 38A:
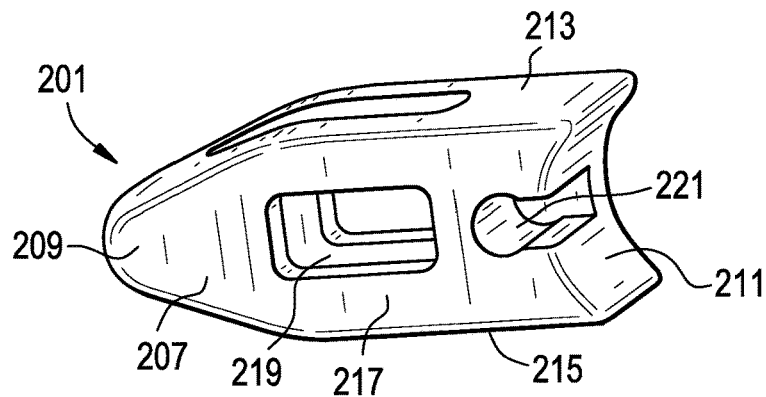
FIGS. 38a-c disclose distal intermediate and proximal cage components of an embodiment of the present invention.
Figure 38B:
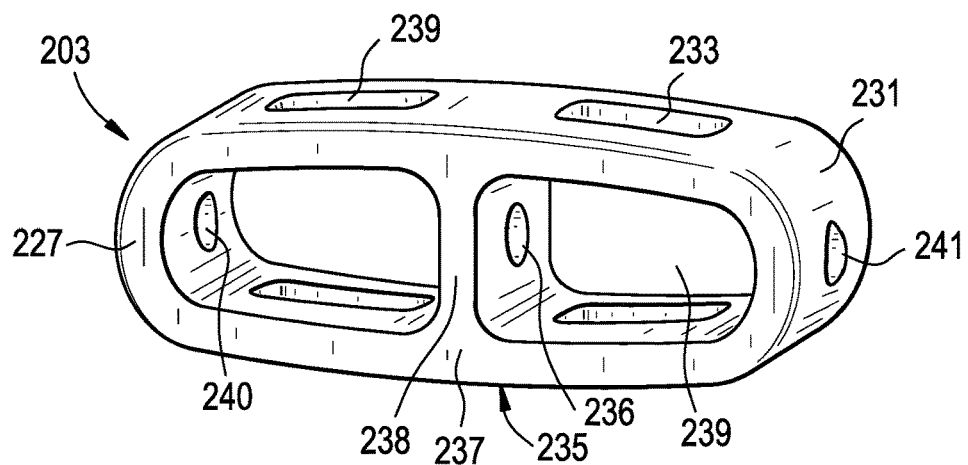
Figure 38C:
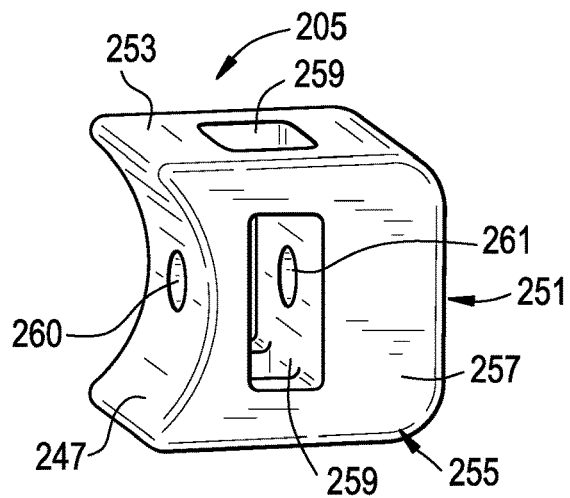

FIGS. 38*a-c* disclose distal intermediate and proximal cage components of an embodiment of the present invention. In particular, there is provided distal cage 201, intermediate cage 203 and proximal cage 205, each of which generally has a cage-like construction.

Distal cage 201 has a distal wall 207 having a bullet nose 209 and a proximal wall 211 having a generally concave shape. It further has an upper wall 213, a lower wall 215, an anterior wall 217, and a posterior wall (not shown), with each of these having a fusion-promoting opening 219 therethrough. Lastly, distal cage 201 has a slot 221 opening upon both its proximal and anterior walls. This slot is adapted to receive the wire of the assembly. Alternative, the slot may be replaced with a partially threaded hole that is unthreaded at its end.

Intermediate cage 203 has a distal wall 227 having a convex shape and a proximal wall 231 having a generally convex shape. It further has an upper wall 233, a lower wall 235, a anterior wall 237, and a posterior wall (not shown), with each of these having a fusion-promoting opening 239 therethrough. Intermediate cage 203 further has a distal throughhole 240 opening through its distal wall, a vertical cross bar 238 extending between the upper and lower walls and having a throughhole 236 therethrough, and a proximal throughhole 241 opening through its proximal wall. These throughholes 240, 236 and 241 are adapted to receive the wire of the assembly.

Proximal cage 205 has a distal wall 247 having a concave shape and a generally flat proximal wall 251. It further has an upper wall 253, a lower wall 255, an anterior wall 257, and a posterior wall (not shown), with each of these having a fusion-promoting opening 259 therethrough. Proximal cage further has a distal throughhole 260 opening through its distal wall, and a proximal throughhole 261 opening through its proximal wall. These throughholes 260,261 are adapted to receive the wire of the assembly.

FIGS. 38*d-g* disclose various steps of the stepwise construction of an intradiscal assembly of the present invention having three cage components and a wire passing therethrough.

Figure 38D:
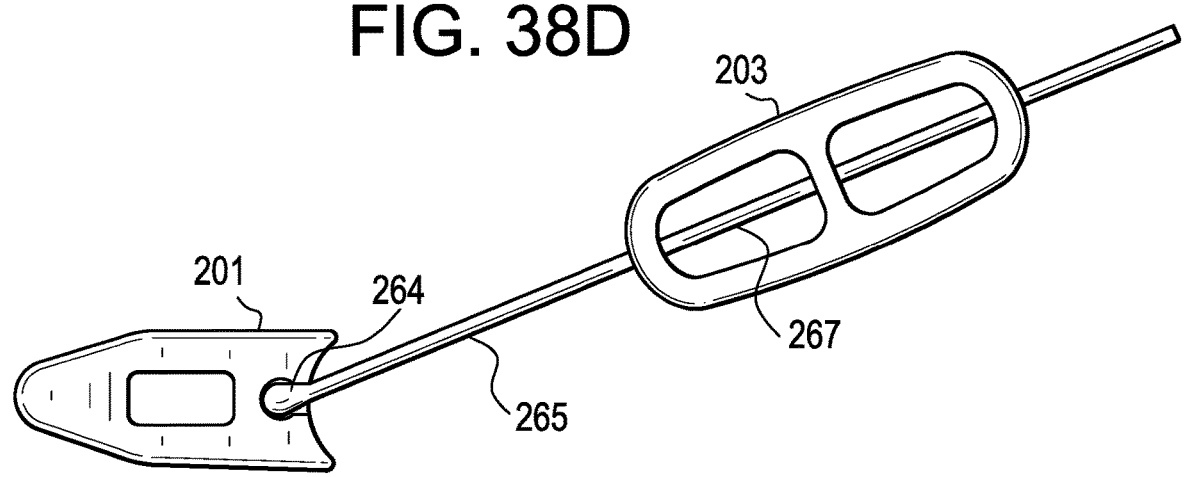
FIGS. 38d-g disclose various views of the stepwise construction of an assembly of the present invention having three cage components and a wire passing therethrough.

FIG. 38*d* shows the distal end 264 of wire 265 received in the slot on the proximal wall of the distal (leading) cage. Intermediate cage 203 is passing over a distal end portion 267 of the wire. This intermediate cage will next be advanced distally to contact the distal cage.

Figure 38E:
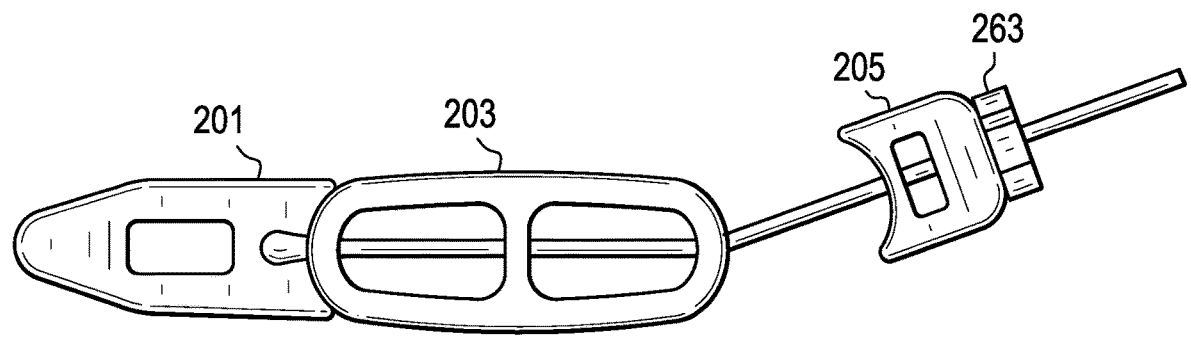

FIG. 38*e* shows the distal end portion of wire received in the slot on the proximal wall of the distal (leading) cage and the intermediate cage. This corresponds to the configuration when both the distal and intermediate cages are in the disc space. The proximal cage is passing over a more proximal portion of the wire. Immediately proximal to the proximal cage is a threaded clamp 263. The function of the threaded clamp is to secure the wire after final assembly and hold the construct together while allowing flexibility between the mating convex/concave surfaces of the cages. This could be accomplished with a wire termination feature or a sleeve abutment that holds the cages together. This proximal cage will next be advanced distally to contact the intermediate cage.

Figure 38F:
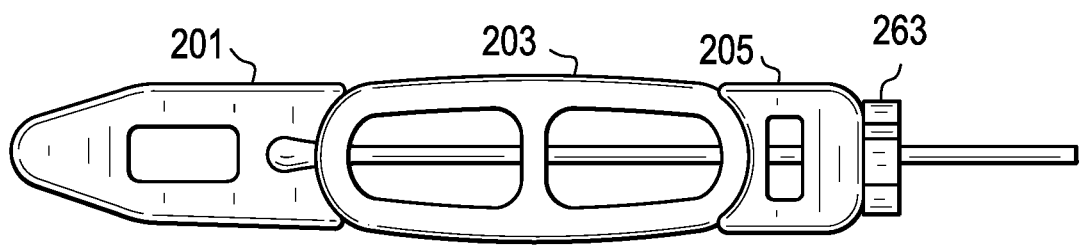

FIG. 38*f* shows the distal end portion of wire received in the slot on the proximal wall of the distal (leading) cage, in the intermediate cage and in the proximal cage. This corresponds to the desired configuration when the entire fusion device is assembled within the disc space.

Figure 38G:
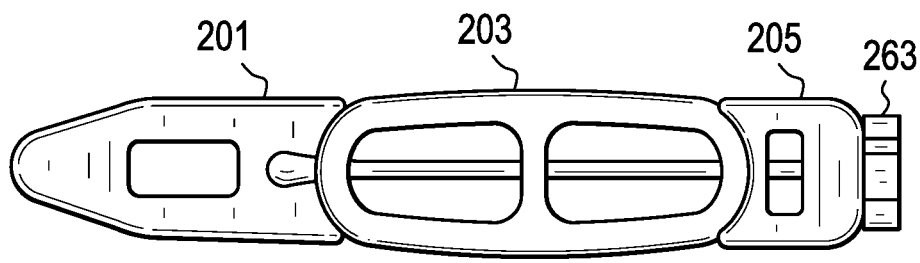

FIG. 38*g* shows that the portion of the wire proximal to the threaded clamp has been separated from the remainder of the wire, so that the wire remains only within the fusion device and the assembly becomes an implant.

Figure 39:
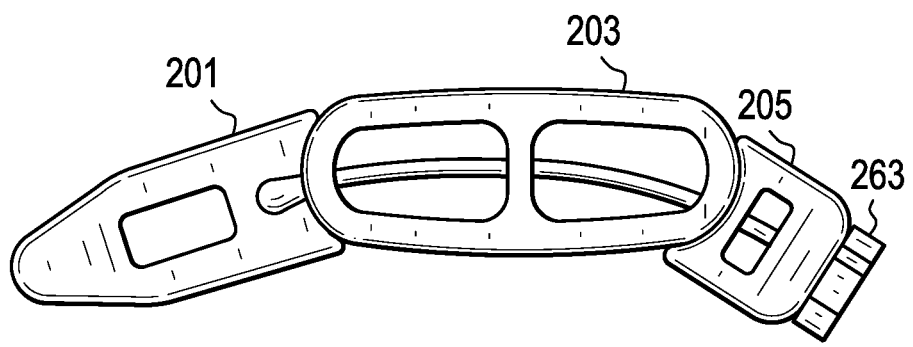
FIG. 39 discloses an over-the-wire fusion device of the present invention configured in an arc.

FIG. 39 discloses the assembly of FIG. 38*g* with the cages forming an arc in the vertical direction. The purpose of this arc is to compensate for uneven endplates. In other embodiments, the curve is in the anterior-posterior direction to better hug the anterior rim of the endplate like a curved TLIF cage.

Figure 40A:
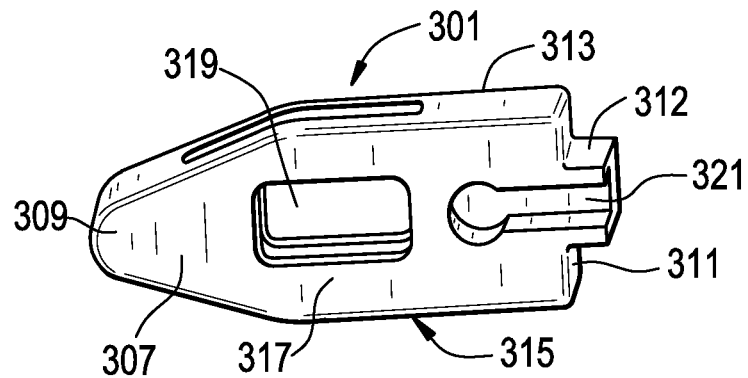
FIGS. 40a-c disclose distal intermediate and proximal cage components of a taper lock embodiment of the present invention.
Figure 40B:
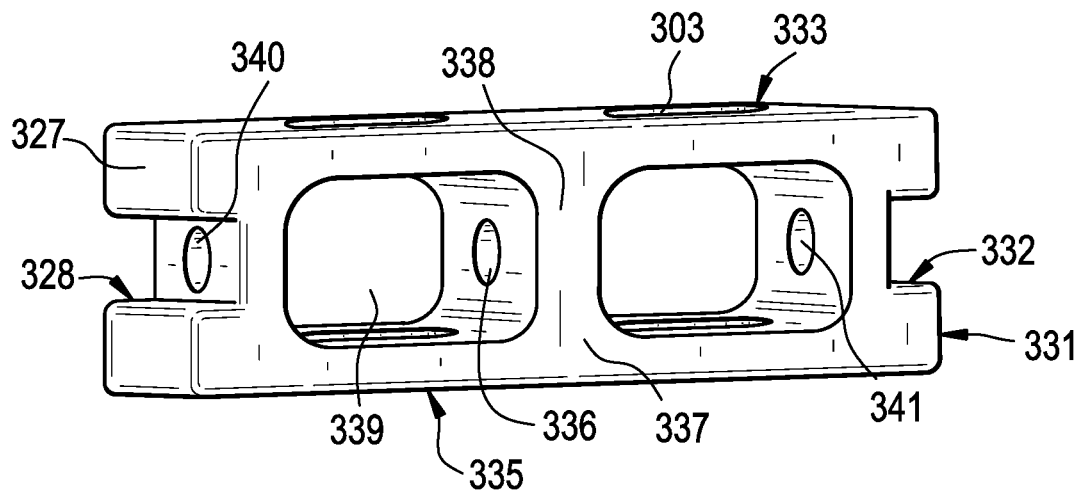
Figure 40C:
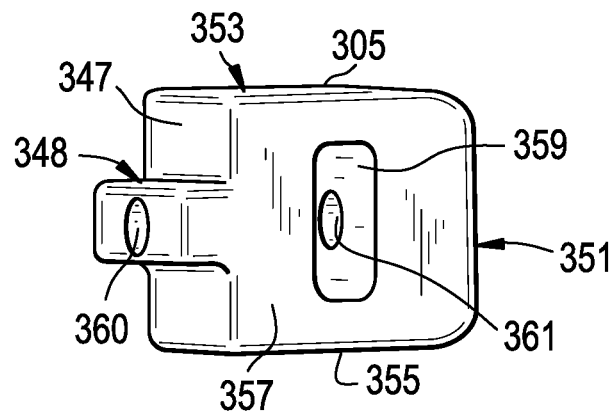

FIGS. 40*a-c* disclose distal, intermediate and proximal cage components of another embodiment of the present invention in which the cage components are joined by taper lock interfaces. In particular, there is provided distal cage 301, intermediate cage 303 and proximal cage 305, each of which generally has a cage-like construction.

Distal cage 301 has a distal wall 307 having a bullet nose 309 and a proximal wall 311 having a tapered projection 312. It further has an upper wall 313, a lower wall 315, an anterior wall 317, and a posterior wall (not shown), with each of these having a fusion-promoting opening 319 therethrough. Lastly, distal cage 301 has a slot 321 opening upon both its proximal and anterior walls. This slot is adapted to receive the wire of the assembly.

Intermediate cage 303 has a distal wall 327 having a tapered recess 328 and a proximal wall 331 having a tapered recess 332. It further has an upper wall 333, a lower wall 335, a anterior wall 337, and a posterior wall (not shown), with each of these having a fusion-promoting opening 339 therethrough. Intermediate cage 303 further has a distal throughhole 340 opening through its distal wall, a vertical cross bar 338 extending between the upper and lower walls and having a throughhole 336 therethrough, and a proximal throughhole 341 opening through its proximal wall. These throughholes 340, 336 and 341 are adapted to receive the wire of the assembly.

Proximal cage 305 has a distal wall 347 having a tapered projection 348 and a generally flat proximal wall 351. It further has an upper wall 353, a lower wall 355, an anterior wall 357, and a posterior wall (not shown), with each of these having a fusion-promoting opening 359 therethrough. This slot is adapted to receive the wire of the assembly. Proximal cage further has a distal throughhole 360 opening through its distal wall, and a proximal throughhole 361 opening through its proximal wall. These throughholes 360, 361 are adapted to receive the wire of the assembly.

Figure 40D:
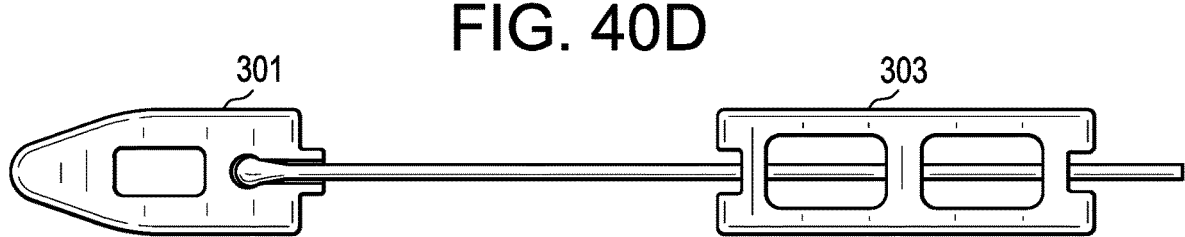
FIGS. 40 d-g disclose various views of the stepwise construction of an assembly of the present invention having three taper lock cage components and a wire passing therethrough.
Figure 40E:
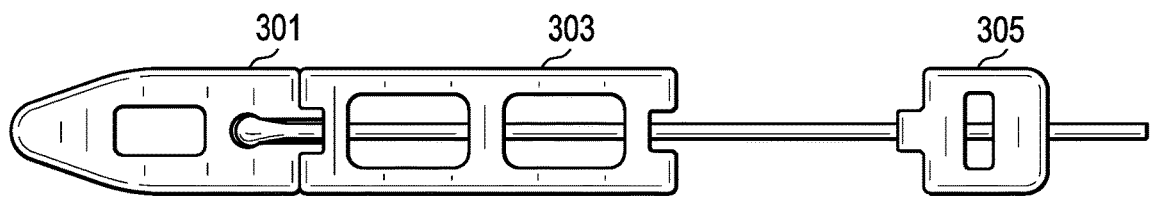
Figure 40F:
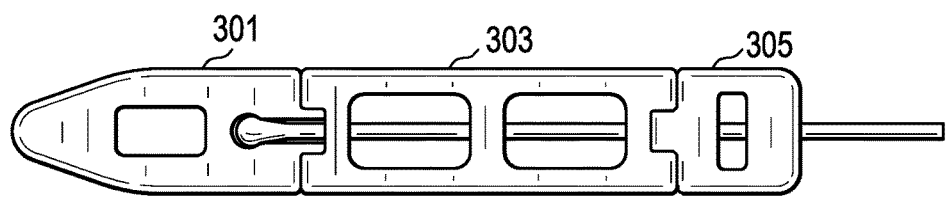
Figure 40G:
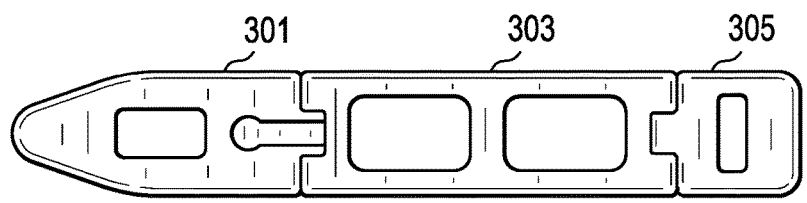

FIGS. 40*d-f* correspond to the steps shown in FIGS. 38D-F, but for cage components having tapered projections and recesses, wherein the tapered projections and recesses on adjacent cages form a taper lock to fix the cage configuration. FIG. 40G discloses the taper locked cage configuration.

In some embodiments of the present invention, an intermediate cage is characterized by asymmetry about its midline—that is, the cage has either mateable projections at both ends or mateable recesses at both ends.

In some embodiments, the leading and/or trailing cages of an assembly may be solid (i.e., like a ramp) and thus are not capable of holding bone graft material. Typically, fusion cages are made in a manner so that the internal surfaces thereof are relatively smooth. However, the smoothness of these surfaces may help bone graft fall out from the cage during handling. Therefore, in some embodiments, the cages are adapted to better hold graft material.

Figure 41A:
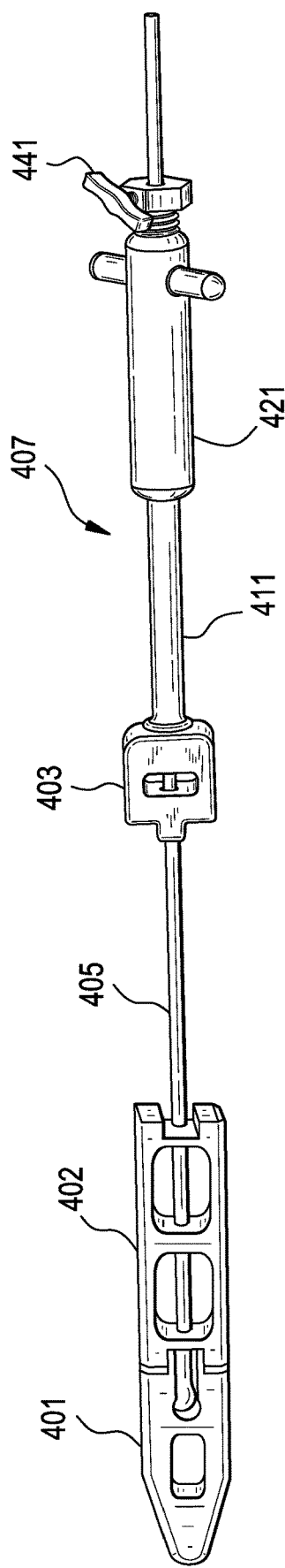
FIGS. 41a-c disclose an insertion device coupled to cages of the present invention.
Figure 41B:
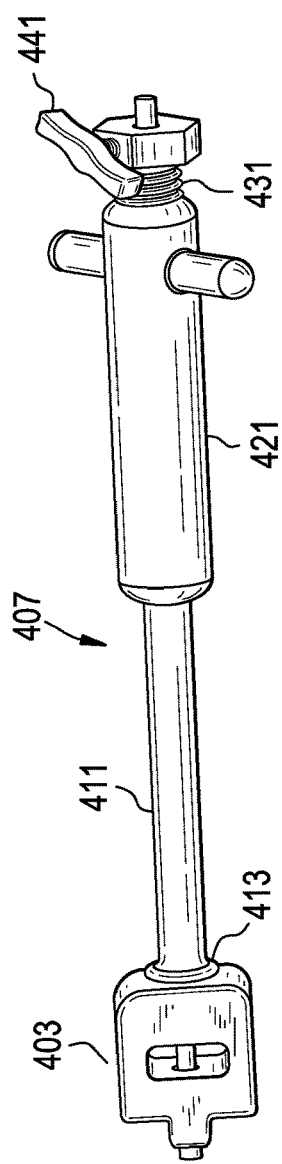
Figure 41C:
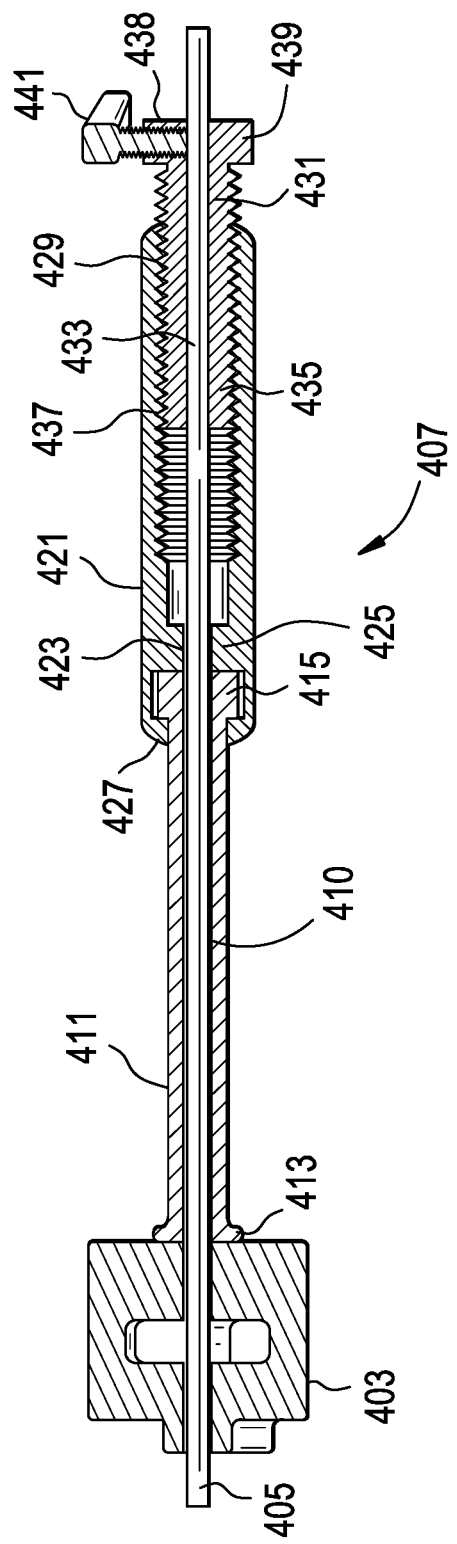

FIGS. 41*a-c* disclose cage components of the present invention coupled with an advancement instrument.

Now referring to FIGS. 41*a-c*, there is provided cage components 401-403 having a guidewire 405 passing therethrough. Attached to the proximal end of cage component 403 and receiving the proximal portion of the guidewire is the advancement instrument 407. The advancement instrument comprises:
  a) a translating sleeve 411 having a bore 410 therethrough, and comprising an enlarged distal end 413 adapted to abutting the cage component and a proximal end 415;
  b) a rotating sleeve 421 having a bore 423 therethrough, the bore defining an annulus 425 having a distal recess 427 therein opening onto the distal end of the rotating sleeve and a proximal threaded recess 429 therein opening onto the proximal end of the rotating sleeve, c) a threaded barrel 431 having a bore 433 therein, a distal end portion 435 having a threaded outer surface 437 and a proximal end portion 439 having at least one transverse throughole 438 therein extending to the bore of the threaded barrel;

d) a set screw 441 received in the transverse throughhole of the threaded barrel and extending to the bore of the threaded barrel;

wherein the proximal end of the translating sleeve is received in the distal recess of the rotating sleeve, and wherein the distal end portion of the threaded barrel is received in the proximal threaded recess of the rotating sleeve.

Typically, the translating sleeve is made of a flexible plastic that can accommodate a curved, lateral trajectory into lower lumbar discs.

In using the instrument with the cages of the present invention, the surgeon typically performs the following steps:

1) sliding a cage component onto the guidewire;
2) sliding the instrument onto the guidewire so that the guidewire is received in each of the throughbores of the instrument;
3) tightening down the set screw in order to secure the threaded barrel to the guidewire;
4) rotating the handles of the rotating sleeve, thereby causing the rotating sleeve to advance distally down the threaded barrel and pushing the translating sleeve distally and thus the cage distally down the guidewire;
5) continuing this rotating action until the cage component is distally advanced to the desired position.

Therefore, this instrument provides the surgeon with a way of incrementally advancing the cage component to a taper-locked position in the disc space in a safe and controlled manner without having to impact the cage component about the guidewire.

It has been noted that the interior surfaces of interbody cages and vertebral body replacements are typically made of machined or molded surfaces, and these surfaces are typically very smooth. Although the smooth surface provides high strength, it does very little to retain the bone graft material that is often inserted into the cage.

Therefore, it is now contemplated to provide textured surfaces or projections upon the inner surfaces of the cage. These projections project into the graft volume, thus providing a mechanical resistance to graft along the interior face. These projections will help maintain the bone graft material in the cage. This technique could be especially advantageous in cases where there is no side window, such as where a graft window could decrease mechanical strength, or in cages holding a large graft volume.

Alternative inner surface designs having projections or coarse texture could be easily manufactured and require no additional steps to perform during surgery.

In some embodiments, the inner surface of the cage is machined to possess a coarse surface roughness Ra of at least 100 µm, more preferably a coarse surface roughness of at least 500 µm, more preferably a coarse surface roughness of at least 1 mm. These surfaces may be characterized as coarse surfaces.

In other embodiments, the inner surface of the cage has a plurality of teeth molded thereon. The height of such teeth may be in the range of about 0.5 mm to about 3 mm. The shapes of such teeth may include, sqauare, scalloped and triangular. The teeth may run linearly in a parallel fashion to the upper and lower surfaces of the cage, as shown below. Alternatively, the teeth may extend at an angle to the upper and lower surfaces, either in a repeating manner, as showin below:

a) - - - - - - -
   - - - - - - -; or
b) / / / / / /
   / / / / / /, or
c) /\/\/\/\
   /\/\/\/\, or
d) / / / / / /
   \ \ \ \ \ \.

In such toothed embodiments, it is contemplated that an inner wall may a matrix of teeth characterized by about 2-3 teeth traversing its height and about 4-6 teeth spanning its length.

In some embodiments, the cage may have a first inner wall having either a coarse surface or teeth projecting therefrom, and a second wall that is relatively smooth. In such embodiments, it is preferable that the smooth surface occupy a windowless wall.

In other embodiments, the cage's inner surfaces may have both a coarse texture and teeth.

Therefore, in accordance with the present invention, there is provided an intervertebral fusion cages, comprising:
  a) upper and lower surfaces adapted for engaging upper and lower vertebral bodies, each comprising a throughhole;
  b) a plurality of sidewalls connecting the upper and lower surfaces, each sidewall comprising an inner surface so that the plurality of sidewalls define an inner chamber; and
wherein at least one inner surface has either a coarse surface roughness Ra or a projection extending therefrom.

We claim:

1. A method of implanting an intervertebral fusion device in a disc space in a patient, comprising the steps of:
   creating an access path to the disc space wherein the access path is substantially in a coronal plane and has an elbowed portion;
   advancing the intervertebral fusion device through the access path, wherein the device bends substantially in a coronal plane while in the elbowed portion of the access path;
   implanting the intervertebral fusion device in the disc space,
   wherein the intervertebral fusion device comprises first and second cages and a tether, each cage comprising:
     a) an anterior wall,
     b) a posterior wall, and
     c) proximal and distal end walls connecting the anterior and posterior walls,
   wherein the proximal end wall of the first cage is fixedly secured to the distal end wall of the second cage by a snap-connection,
   wherein each cage has at least one hole passing therethrough, and the tether is received through at least one hole in each cage,
   and wherein the entire tether is removed from the cages after the snap-connection between cages is made.

* * * * *